(12) United States Patent
Minai

(10) Patent No.: US 7,686,757 B2
(45) Date of Patent: Mar. 30, 2010

(54) POSITION DETECTING APPARATUS, BODY-INSERTABLE APPARATUS SYSTEM, AND POSITION DETECTING METHOD

(75) Inventor: Tetsuo Minai, Hachioji (JP)

(73) Assignee: Olympus Corporation, Tokyo (JP)

( * ) Notice: Subject to any disclaimer, the term of this patent is extended or adjusted under 35 U.S.C. 154(b) by 389 days.

(21) Appl. No.: 11/631,234

(22) PCT Filed: Sep. 13, 2005

(86) PCT No.: PCT/JP2005/016826

§ 371 (c)(1),
(2), (4) Date: Dec. 29, 2006

(87) PCT Pub. No.: WO2006/030773

PCT Pub. Date: Mar. 23, 2006

(65) Prior Publication Data

US 2007/0255087 A1 Nov. 1, 2007

(30) Foreign Application Priority Data

Sep. 13, 2004 (JP) ............................. 2004-266066

(51) Int. Cl.
*A61N 2/00* (2006.01)
(52) U.S. Cl. ........................................ 600/12; 128/899
(58) Field of Classification Search ................ 128/897, 128/899; 600/9–15
See application file for complete search history.

(56) References Cited

U.S. PATENT DOCUMENTS 5,681,260 A * 10/1997 Ueda et al. .................. 600/114

(Continued)

FOREIGN PATENT DOCUMENTS

JP 2003-19111 1/2003

(Continued)

OTHER PUBLICATIONS

Nagaoka et al., "Development of a small wireless position sensor for medial capsule devices", Proceedings of the 26th Annual International Conference of the IEEE Engineering in Medicine and Biology Society, vol. 3, Sep. 1-5, 2004, pp. 2137-2140.

(Continued)

*Primary Examiner*—Charles A Marmor, II
*Assistant Examiner*—Christine D Hopkins
(74) *Attorney, Agent, or Firm*—Scully, Scott, Murphy & Presser, P.C.

(57) ABSTRACT

A position detecting apparatus 3 includes receiving antennas 7a to 7d to receive a radio signal, transmitting antennas 8a to 8d to transmit a radio signal for power supply to a capsule endoscope 2, a first linear magnetic field generator 9 that generates a first linear magnetic field, a second linear magnetic field generator 10 that generates a second linear magnetic field, a diffuse magnetic field generator 11 that generates a diffuse magnetic field, a processing device 12 that performs a predetermined process on the radio signal received through the receiving antennas 7a to 7d, and a magnetic field sensor 13 that functions as a body-size information detector. The magnetic field sensor 13 has a function of detecting magnetic field strength at an arranged position as body-size information, and the processing device 12 has a function of controlling the first linear magnetic field generator 9 and the like based on the magnetic field strength detected by the magnetic field sensor 13. Thus, the position detecting apparatus is realized that is capable of generating a magnetic field for position detection having an optimal strength according to a difference in body sizes of subjects.

5 Claims, 14 Drawing Sheets

U.S. PATENT DOCUMENTS

| | | | |
|---|---|---|---|
| 5,729,129 A | | 3/1998 | Acker |
| 6,138,681 A | * | 10/2000 | Chen et al. .................. 128/899 |
| 6,233,476 B1 | | 5/2001 | Strommer et al. |
| 6,904,308 B2 | | 6/2005 | Frisch et al. |
| 2003/0199756 A1 | | 10/2003 | Kawashima |

FOREIGN PATENT DOCUMENTS

| | | |
|---|---|---|
| JP | 2003-305044 A | 10/2003 |
| JP | 2004-89421 A | 3/2004 |

OTHER PUBLICATIONS

Extended Supplementary Partial European Search Report dated Nov. 20, 2009.

* cited by examiner

POSITION DETECTING APPARATUS, BODY-INSERTABLE APPARATUS SYSTEM, AND POSITION DETECTING METHOD

TECHNICAL FIELD

The present invention relates to a position detecting apparatus that detects a position of a detection subject using a magnetic field for position detection of which strength is position dependent, a body-insertable apparatus system that applies the position detection, and a position detecting method.

BACKGROUND ART

Recently, in the field of endoscope, a swallowable capsule endoscope has been proposed. In this capsule endoscope, an imaging function and a radio communication function are provided. The capsule endoscope has a function of sequentially taking images after the capsule endoscope is swallowed from a mouth of a patient (a human body) for observation (examination) until it is naturally discharged, while passing through body cavities, for example, internal organs such as a stomach and a small intestine, according to the peristalsis thereof.

Image data obtained inside the body by the capsule endoscope while moving inside the body cavities is sequentially transmitted to the outside by radio communication, and stored in a memory externally provided. If the receiver having the radio communication function and the memory function is carried, the subject can freely act during whole period from swallow of the capsule endoscope until discharge thereof. After the capsule endoscope is discharged, doctors and nurses can perform diagnosis based on the image data stored in the memory by displaying an image of the organs on a display (for example, see Patent Document 1).

Furthermore, among conventional capsule endoscope systems, there has been proposed a system provided with a mechanism to detect a position of the capsule endoscope inside a body cavity. For example, a magnetic field of which strength is position dependent is generated inside the body of a subject to which the capsule endoscope is introduced, and based on the strength of the magnetic field that is detected by a magnetic field sensor provided in the capsule endoscope, position of the capsule endoscope inside the body of the subject can be detected. In the capsule endoscope system, such a configuration is adopted that a predetermined coil is arranged to generate the magnetic field, and by feeding a predetermined electric current to this coil, the magnetic field is generated inside the body of the subject. In this case, because it is difficult to detect a position of the capsule endoscope in advance, the magnetic field to be generated should be strong enough to enable detection by the capsule endoscope in all areas in which the capsule endoscope is possible to be positioned inside the body of the subject. Specifically, in the conventional capsule endoscope systems, the magnetic field with which detection by the capsule endoscope can be achieved in all digestive organs from the buccal cavity to the anus is generated.

Patent Document 1: Japanese Patent Application Laid-open No. 2003-19111

DISCLOSURE OF INVENTION

Problem to be Solved by the Invention

However, in the conventional capsule endoscope system having the position detection mechanism, there is a problem that power consumption greatly increases. In other words, to generate the magnetic field of which strength is position dependent inside the body of the subject, it is necessary to keep providing a large electric current to the coil for several hours to more than ten hours during the capsule endoscope is located inside the body of the subject. Particularly in the conventional capsule endoscopes, the magnetic field that is strong enough to enable detection by the capsule endoscope in all digestive organs inside the body of the subject as described above, and therefore, power required for generation of the magnetic field is tremendous.

Furthermore, in the capsule endoscope system, a difference in body sizes of subjects is a problematic issue. In other words, for example, a male adult and an infant significantly differ in body size, and therefore, an area of regions in which the magnetic field for position detection is necessary to be generated is totally different. In the conventional capsule endoscope system, however, the magnetic field for position detection is uniformly generated regardless of the difference in the body sizes of the subjects. Therefore, for example, the magnetic field is generated in unnecessarily wide area for an infant, thereby consuming unnecessary power, and a problem occurs such that a disadvantageous effect is caused on electronic devices and the like therearound.

The present invention has been achieved in view of the above problems, and an object of the invention is to realize a position detecting apparatus that is capable of generating the magnetic field for position detection of an optimal strength depending on the body size of a subject, a body-insertable apparatus that uses the position detecting apparatus, and a position detecting method, with respect to position detecting apparatuses and the like that perform position detection of a detection subject such as the capsule endoscope, using the magnetic field for position detection of which strength is position dependent.

Means for Solving Problem

A position detecting apparatus according to one aspect of the present invention performs position detection of a detection subject using a predetermined magnetic field for position detection, and includes a magnetic field generator that generates the magnetic field for position detection; a magnetic field sensor that detects strength of the magnetic field for position detection at a position distant from the magnetic field generator by a distance that is equal to or more than a maximum value of a distance between an area in which the detection subject can be positioned and the magnetic field generator; a magnetic-field strength controller that controls the strength of the magnetic field for position detection that is generated by the magnetic field generator, based on a detection result by the magnetic field sensor; and a position calculator that calculates a position of the detection subject using the strength of the magnetic field for position detection detected at a position at which the detection subject is present.

According to the position detecting apparatus as above, the magnetic-field strength controller is provided that controls the strength of the magnetic field for position detection based on the detection result by the magnetic field sensor that is arranged at a position further than the magnetic field generator from an arbitrary point in the area in which the detection subject is possible to be positioned. Therefore, it is possible to maintain the strength of the magnetic field for position detection inside the area at a certain level at all times regardless of a change of the area in which the detection subject is possible to be positioned.

Moreover, in the position detecting apparatus, the magnetic-field strength controller controls the magnetic field generator such that the magnetic field strength detected by the magnetic field sensor takes a value equal to or higher than a magnetic field strength that is detectable by the detection subject.

Furthermore, in the position detecting apparatus, the detection subject may be a body-insertable apparatus that is introduced into a predetermined subject, and the magnetic field sensor may be arranged on an outer surface of the subject.

Moreover, a body-insertable apparatus system according to another aspect of the present invention includes a body-insertable apparatus that is introduced into a subject and moves inside the subject, and a position detecting apparatus that detects a position of the body-insertable apparatus inside the subject using a predetermined magnetic field for position detection, wherein the body-insertable apparatus includes a magnetic field sensor that detects strength of the magnetic field for position detection at a position at which the body-insertable apparatus is present, and a radio transmitting unit that transmits a radio signal that contains information on the strength of the magnetic field detected by the magnetic field sensor, and the position detecting apparatus includes a magnetic field generator that generates the magnetic field for position detection, and a magnetic-field strength controller that controls the strength of the magnetic field for position detection generated by the magnetic field generator, based on body-size information that corresponds to a shape of an outer surface of the subject.

According to the body-insertable apparatus system as above, since the magnetic-field strength controller is provided that controls the strength of the magnetic field for position detection generated by the magnetic field generator based on the body-size information that varies corresponding to the difference in body sizes of subjects, it is possible to generate the magnetic field for position detection having a predetermined strength in an area inside the subject regardless of the difference in body sizes and the like.

Furthermore, in the body-insertable apparatus system, the magnetic-field strength controller may control a driving condition of the magnetic field generator so that the magnetic field for position detection has strength detectable by the magnetic field sensor in all areas in which the body-insertable apparatus can be positioned inside the subject, based on the body-size information.

Moreover, the body-insertable apparatus system may further include a body-size information detector that detects the body-size information, and the magnetic-field strength controller may control the strength of the magnetic field for position detection that is generated by the magnetic field generator, based on the body-size information detected by the body-size information detector.

Furthermore, in the body-insertable apparatus system, the body-size information detector may be arranged at a predetermined position on the outer surface of the subject, and may include a magnetic field sensor unit that detects strength of the magnetic field for position detection at the arranged position as the body-size information, and the magnetic-field strength controller may control such that the magnetic field strength detected as the body-size information has strength detectable by the magnetic field sensor in the body-insertable apparatus.

Moreover, in the body-insertable apparatus system, the magnetic field generator may include a coil that generates a magnetic field according to power supplied by a predetermined power supply unit, and the magnetic-field strength controller may control strength of the magnetic field for position detection by adjusting power to be supplied to the coil.

Furthermore, in the body-insertable apparatus system, the magnetic field generator may include a coil that generates a magnetic field according to power supplied by a power supply unit constituted of any one of a primary cell and a secondary cell, and the body-insertable apparatus system may further include a power determining unit that determines whether the power supply unit is capable of supplying power for a predetermined period, the power corresponding to the magnetic field for position detection having the magnetic field strength acquired by the magnetic-field strength controller; and a display unit that displays a determination result acquired by the power determining unit.

Moreover, a position detecting method according to still another aspect of the present invention is a position detecting method of detecting a position of a body-insertable apparatus that is introduced into a subject and that moves inside the subject using a predetermined magnetic field for position detection, and includes a magnetic-field strength detecting step of detecting strength of the magnetic field for position detection at a predetermined position on an outer surface of the subject; a magnetic-field strength control step of controlling the strength of the magnetic field for position detection based on the magnetic field strength detected at the magnetic-field strength detecting step; and a position detecting step of detecting a position of the detection subject based on the strength of the magnetic field for position detection of which the strength is controlled at the magnetic-field strength control step at a position at which the detection subject is present.

Since the magnetic-field strength control step is included at which the strength of the magnetic field for position detection is controlled based on the magnetic field strength detected at the magnetic-field strength detecting step on the outer surface of the subject, it is possible to generate the magnetic field for position detection optimized for the position detection of the body-insertable apparatus that is present inside the subject.

Furthermore, in the position detecting method the magnetic field for position detection may be generated by a coil to which power is supplied by a power supply unit that is constituted of any one of a primary cell and a secondary cell, and the position detecting method may further include a determining step of determining whether an amount of retained power that is retained in the power supply unit is sufficient for an amount of a necessary power that is necessary for generating the magnetic field for position detection controlled at the magnetic-field strength control step.

EFFECT OF THE INVENTION

Since the position detecting apparatus according to the present invention is configured to include the magnetic-field strength controller that controls the strength of the magnetic field for position detection based on the detection result by the magnetic field sensor that is arranged at a position further than the magnetic field generator from an arbitrary point in the area in which the detection subject is possible to be positioned, it is possible to maintain the strength of the magnetic field for position detection inside the area at a certain level at all times regardless of a change of the area in which the detection subject is possible to be positioned.

Moreover, since the body-insertable apparatus system according to the present invention is configured to include the magnetic-field strength controller that controls the strength of the magnetic field for position detection using the body-size information that varies corresponding to the difference in body sizes of subjects, it is possible to generate the magnetic field for position detection having a predetermined strength in an area inside the subject regardless of the difference in body sizes and the like.

Furthermore, since the position detecting method according to the present invention includes the magnetic-field strength control step of controlling the strength of the magnetic field for position detection based on the magnetic field strength detected at the magnetic-field strength detecting step on the outer surface of the subject, it is possible to generate the magnetic field for position detection optimized for the position detection of the body-insertable apparatus that is present inside the subject.

EXPLANATIONS OF LETTERS OR NUMERALS

Figure 1:
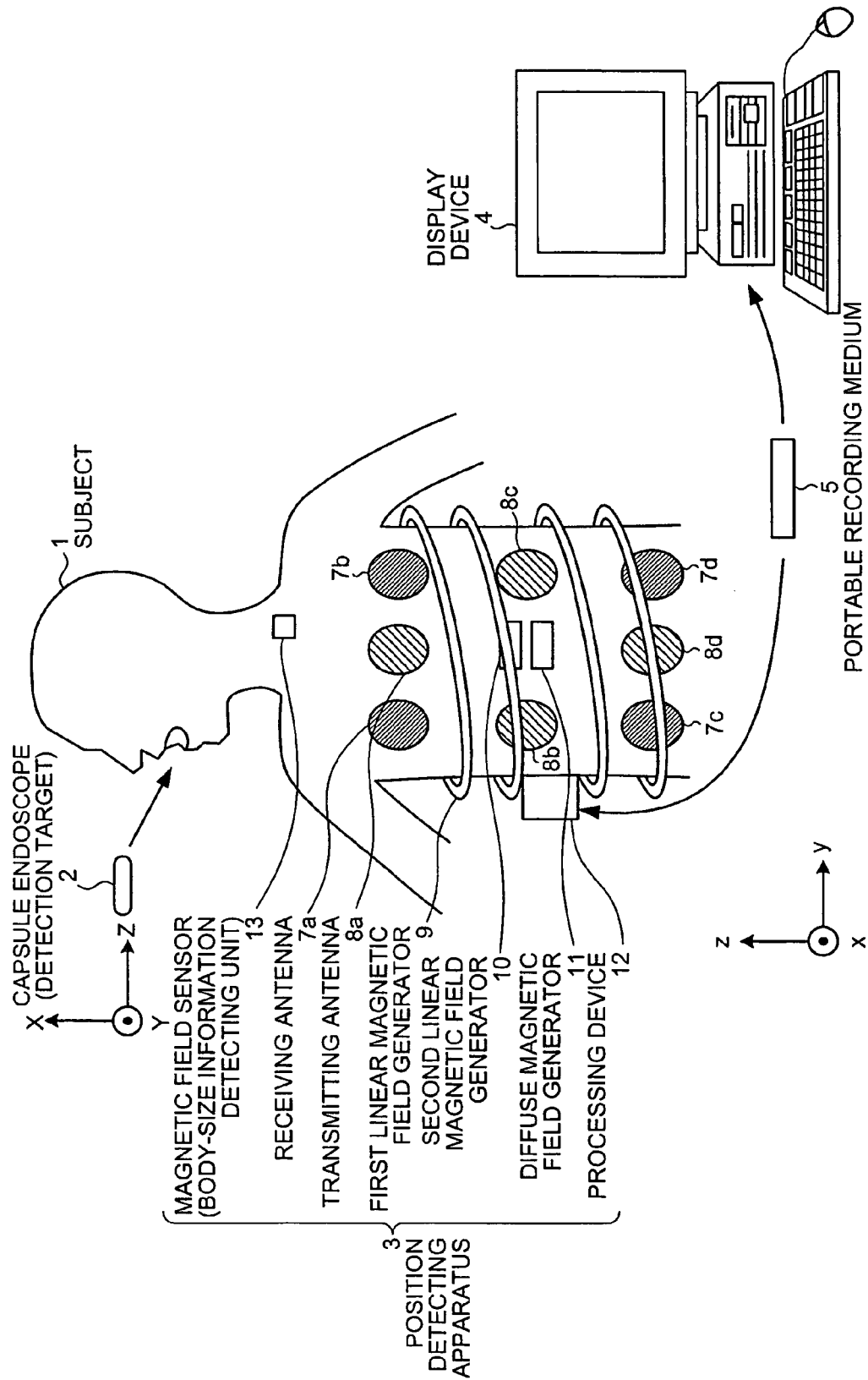
FIG. 1 is a schematic diagram showing an entire configuration of a body-insertable apparatus system according to a first embodiment of the present invention.

1 Subject
2 Capsule endoscope
3, 60 Position detecting apparatus
4 Display device
5 Portable recording medium
7a to 7d, 28 Receiving antenna
8a to 8d, 27 Transmitting antenna
9 First linear magnetic field generator
10 Second linear magnetic field generator
11 Diffuse magnetic field generator
12, 62 Processing device
13, 13a to 13d, 16 Magnetic field sensor
14 In-vivo information acquiring unit
15, 39 Signal processing unit
17 Amplifier
18 A/D converter
19 Radio transmitting unit
20 Switching unit
21 Timing generator
22 LED
23 LED driving controller
24 CCD
25 CCD driving controller
26 Transmitting circuit
29 Power regenerating circuit
30 Booster circuit
31 Capacitor
32, 34 Coil
37 Receiving antenna selector
38 Receiving circuit
40 Orientation calculator
41 Position calculator
42 Magnetic-field line orientation database
44 Oscillator
46 Amplifier circuit
47 Transmitting antenna selector
50 Magnetic-field strength controller
51 Magnetic-field strength database
52 Power determining unit
53 Power supply unit
54 Display unit
56 Possible location area
57 Furthest point
59 Curved surface
61 Earth magnetism sensor
63 Earth-magnetism orientation calculator

BEST MODE(S) FOR CARRYING OUT THE INVENTION

A position detecting apparatus and a body-insertable apparatus system according to best modes for carrying out the invention (hereinafter, simply "embodiment") will be explained below. Note that drawings are schematically shown, a relationship between thickness and width of each part, ratio of thickness of each part differs from actual cases, and needless to mention that also among drawings, in some parts, a relationship and ratio of sizes differ therebetween.

First Embodiment

First, a body-insertable apparatus system according to a first embodiment of the present invention will be explained. FIG. 1 is a schematic diagram showing an entire configuration of the body-insertable apparatus system according to the first embodiment. As shown in FIG. 1, the body-insertable apparatus system according to the first embodiment includes a capsule endoscope 2 that is introduced into the inside of a subject 1 and moves along a passing channel, a position detecting apparatus 3 that performs radio communication with the capsule endoscope 2 and that detects a positional relationship between target coordinate axes fixed to the capsule endoscope 2 and reference coordinate axes fixed to the subject 1, a display device 4 that displays a content of a radio signal transmitted from the capsule endoscope 2, and a portable recording medium 5 to communicate information between the position detecting apparatus 3 and the display device 4. Moreover, as shown in FIG. 1, in the first embodiment, the target coordinate axes that are composed of an X-axis, a Y-axis, and a Z-axis, and that are fixed to the capsule endoscope 2, and the reference coordinate axes that are composed of an x-axis, a y-axis, and a z-axis, and that are set regardless of movement of the capsule endoscope 2, specifically, that are fixed to the subject 1, are provided, and the positional relationship of the target coordinate axes with respect to the reference coordinate axes is detected with a mechanism explained below.

The display device 4 is to display images inside the subject and the like that are imaged by the capsule endoscope 2, and has a configuration such as that of a workstation and the like that performs image display based on data acquired with the portable recording medium 5. Specifically, the display device 4 can be configured to directly display the images and the like with a CRT display, a liquid crystal display, and the like, or can be configured to output the images and the like to other mediums such as a printer.

The portable recording medium 5 is attachable and detachable to a processing device 12 described later and the display device 4, and has a configuration enabling output and record of information when attached to those. Specifically, the portable recording medium 5 is attached to the processing device 12 during the capsule endoscope 2 is moving inside a body cavity of the subject 1 to store the images inside the subject and the positional relationship of the target coordinate axes with respect to the reference coordinate axes. The portable recording medium 5 is configured to be detached from the processing device 12 and then attached to the display device 4 after the capsule endoscope 2 is discharged out of the subject 1, and data stored therein is read out by the display device 4. By performing data communication between the processing device 12 and the display device 4 with the portable recording medium 5 such as a compact flash (registered trademark) memory, the subject 1 can freely act even while the capsule endoscope 2 is moving inside the body of the subject 1, unlike the case in which the processing device 12 and the display device 4 are connected by wire.

The capsule endoscope 2 will be explained next. The capsule endoscope 2 functions as one example of the detection subject in the present invention. Specifically, the capsule endoscope 2 is introduced inside the subject 1, and has functions of acquiring in-vivo information while moving inside the body of the subject 1, and of transmitting a radio signal including the acquired in-vivo information to the outside. Moreover, the capsule endoscope 2 has a function of detecting a magnetic field to detect a positional relationship described later and has a configuration such that a driving power is externally supplied, specifically, a function of receiving a radio signal transmitted from the outside and regenerating the driving power from the received radio signal.

Figure 2:
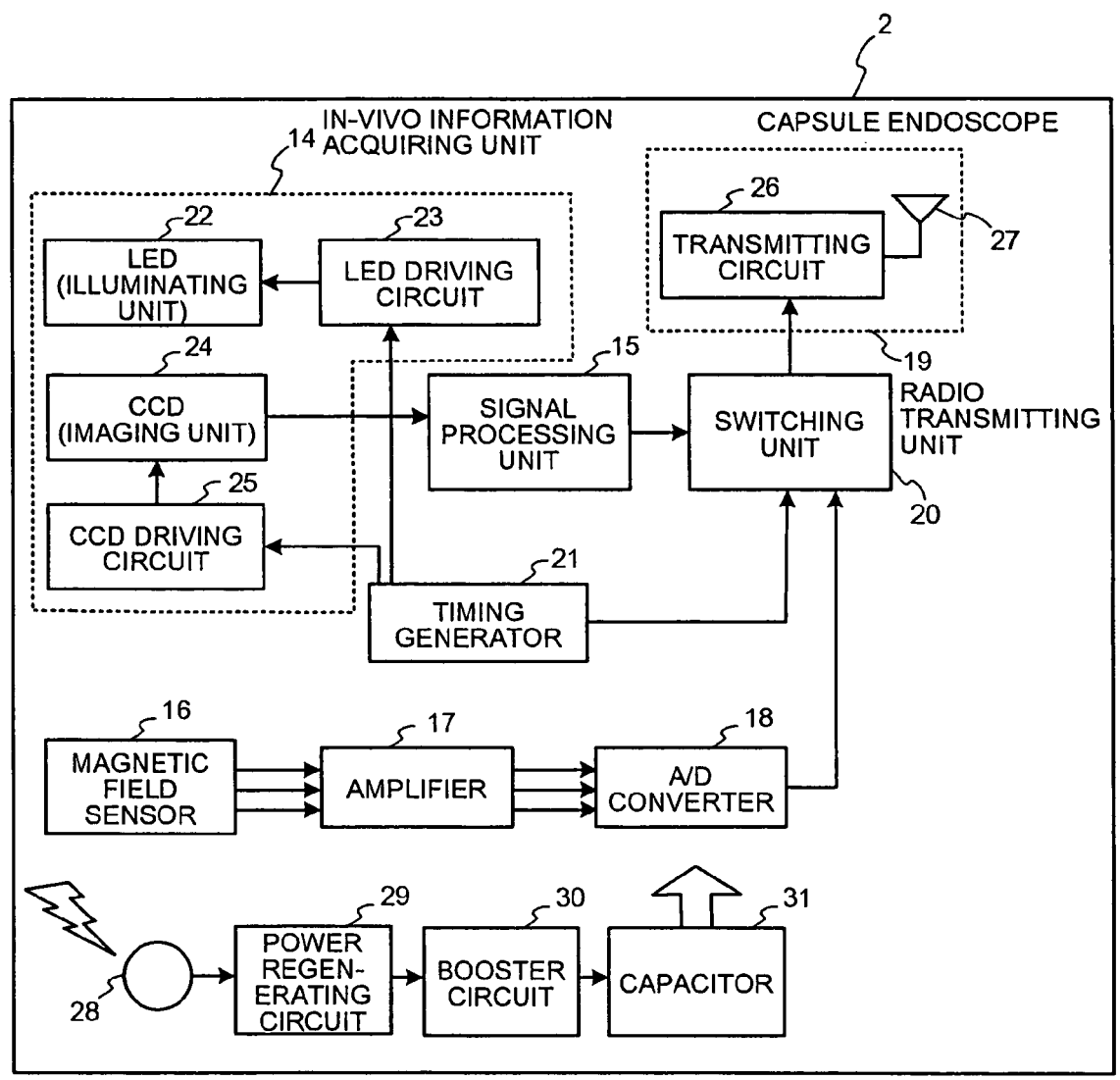
FIG. 2 is a schematic block diagram showing a configuration of a capsule endoscope provided in the body-insertable apparatus system.

FIG. 2 is a block diagram showing a configuration of the capsule endoscope 2. As shown in FIG. 2, the capsule endoscope 2 includes an in-vivo information acquiring unit 14 that acquires in-vivo information as a mechanism to acquire in-vivo information, and a signal processing unit 15 that performs a predetermined process on the acquired in-vivo information. Furthermore, the capsule endoscope 2 includes a magnetic field sensor 16 that detects a magnetic field as a magnetic field detecting mechanism, and that outputs an electrical signal corresponding to the detected magnetic field, an amplifier 17 to amplify the output electrical signal, and an A/D converter 18 that converts the electrical signal output from the amplifier 17 into a digital signal.

The in-vivo information acquiring unit 14 is to acquire in-vivo information, which is, in the first embodiment, an internal image of the subject to be image data of the inside of the subject. Specifically, the in-vivo information acquiring unit 14 includes an LED 22 that functions as an illuminating unit, an LED driving controller 23 that controls driving of the LED 22, a CCD 24 that functions as an imaging unit that acquires an image of at least a part of an area illuminated by the LED 22, and a CCD driving controller 25 that controls a driving condition of the CCD 24. As specific configurations of the illuminating unit and the imaging unit, it is not absolutely necessary to use the LED and the CCD, but, for example, a CMOS and the like can be used as the imaging unit.

The magnetic field sensor 16 is to detect a direction and strength of the magnetic field generated in a location area of the capsule endoscope 2. Specifically, the magnetic field sensor 16 is configured, for example, with an MI (MagnetoImpedance) sensor. The MI sensor has a configuration in which, for example, FeCoSiB amorphous wire is used as a magneto sensing medium, and detects a magnetic field strength utilizing an MI effect in which magnetic impedance of the magneto sensing medium greatly changes due to an external magnetic field when a high frequency electric current is fed to the magneto sensing medium. The magnetic field sensor 16 can be configured with, for example, an MRE (magneto resistance effect) device and a GMR (giant magneto resistance effect) magnetic sensor or the like other than the MI sensor.

As shown also in FIG. 1, as the coordinate axes of the capsule endoscope 2, the target coordinate axes provided with the X-axis, the Y-axis, and the Z-axis are assumed in the first embodiment. Corresponding to the target coordinate axes, the magnetic field sensor 16 has functions of detecting a magnetic field strength of an X direction component, a Y direction component, and a Z direction component for the magnetic field generated in an area in which the capsule endoscope 2 is located, and outputting an electrical signal corresponding to the magnetic field strength of each direction. A magnetic field strength component in the target coordinate axes detected by the magnetic field sensor 16 is output to a position detecting apparatus 3 through a radio transmitting unit 19 described later. The position detecting apparatus 3 calculates a positional relationship between the target coordinate axes and the reference coordinate axes based on a value of a magnetic field component detected by the magnetic field sensor 16.

Moreover, the capsule endoscope 2 includes a transmitting circuit 26 and a transmitting antenna 27, and includes the radio transmitting unit 19 to perform radio transmission to the outside and a switching unit 20 that switches between an output from the signal processing unit 15 and an output from the A/D converter 18 as necessary for a signal to be output to the radio transmitting unit 19. Furthermore, the capsule endoscope 2 includes a timing generator 21 to synchronize driving timing of the in-vivo information acquiring unit 14, the signal processing unit 15, and the switching unit 20.

Moreover, the capsule endoscope 2 includes a receiving antenna 28 as a mechanism to receive, from the outside, a radio signal for power supply, a power regenerating circuit 29 that regenerates power from the radio signal received through the receiving antenna 28, a booster circuit 30 that boosts a voltage of a power signal output from the power regenerating circuit 29, and a capacitor 31 that accumulates the power signal that is changed into a predetermined voltage by the booster circuit 30 to supply to other components described above as driving power.

The receiving antenna 28 is formed with, for example, a loop antenna. The loop antenna is fixed at a predetermined position inside the capsule endoscope 2, and specifically, fixed at a predetermined position in the target coordinate axes that is fixed to the capsule endoscope 2 so as to be directional.

The position detecting apparatus 3 will be explained next. The position detecting apparatus 3 includes transmitting antennas 8a to 8d to receive a radio signal transmitted from the capsule endoscope 2, transmitting antennas 8a to 8d to transmit a radio signal for power supply to the capsule endoscope 2, a first linear magnetic field generator 9 that generates a first linear magnetic field, a second linear magnetic field generator 10 that generates a second linear magnetic field, a diffuse magnetic field generator 11 that generates a diffuse magnetic field, the processing device 12 that performs a predetermined process on the radio signal and the like received through receiving antennas 7a to 7d, and a magnetic field sensor 13 that functions as a body-size information detector.

The receiving antennas 7a to 7d are to receive the radio signal transmitted from the radio transmitting unit 19 provided in the capsule endoscope 2. Specifically, the receiving antennas 7a to 7d are formed with a loop antenna and the like, and have a function of transmitting, to the processing device 12, the received radio signal.

The transmitting antennas 8a to 8d are to transmit the radio signal generated by the processing device 12 to the capsule endoscope 2. Specifically, the transmitting antennas 8a to 8d are formed with a loop antenna and the like that are electrically connected to the processing device 12.

It is necessary to note that specific configurations of the receiving antennas 7a to 7d, the transmitting antennas 8a to 8d, and the first linear magnetic field generator 9 described below or the like are not limited to ones shown in FIG. 1. In other words, the components shown in FIG. 1 are to schematically show the configuration, and the number of the receiving antennas 7a to 7d and the like are not limited to the number shown FIG. 1. The position of arrangement, specific forms, and the like are also not limited to those shown in FIG. 1, and an arbitrary configuration can be adopted.

The first linear magnetic field generator 9, the second linear magnetic field generator 10, and the diffuse magnetic field generator 11 that generate the first linear magnetic field, the second magnetic field, and the diffuse magnetic field respectively that function as the magnetic field for position detection will be explained next. The first linear magnetic field generator 9 is to generate a linear magnetic field in a predetermined direction inside the subject 1. A "linear magnetic field" is a magnetic field constituted of a magnetic field component practically only in one direction in at least a predetermined spatial area, which is a spatial area in which the capsule endoscope 2 can be located inside the subject 1 in the first embodiment. Specifically, as shown in FIG. 1, the first linear magnetic field generator 9 is provided with a coil formed so as to wind around a torso portion of the subject 1, and has a function of generating the linear magnetic field in the spatial area inside the body of the subject 1 by feeding a predetermined power to the coil by a power supply unit (not shown). An arbitrary direction can be selected as a traveling direction of the first linear magnetic field, however, in the first embodiment, the first linear magnetic field is assumed to be a linear magnetic field that travels in a direction of the z-axis of the reference coordinate axes that are fixed to the subject 1.

Figure 3:
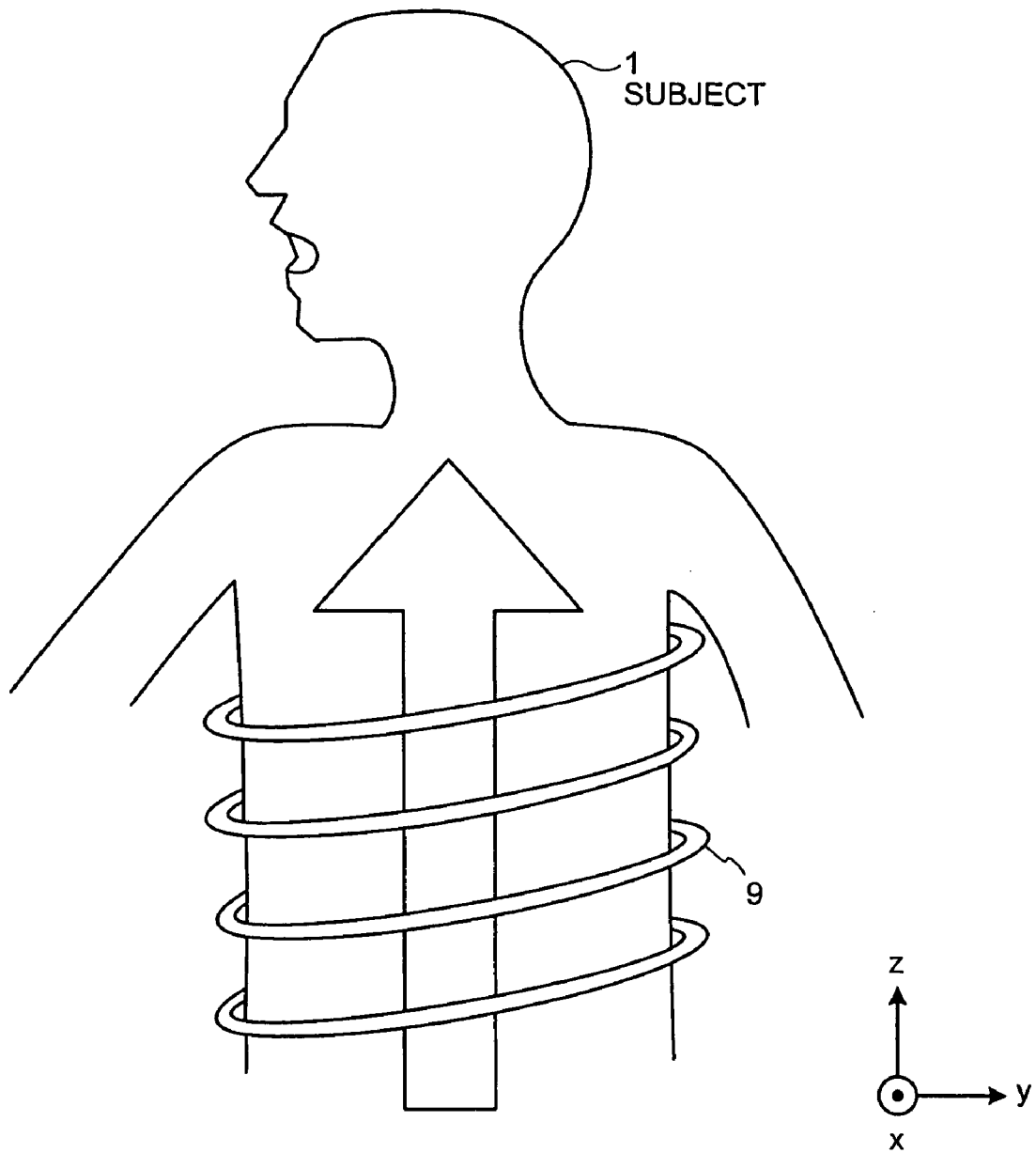
FIG. 3 is a schematic diagram showing a first linear magnetic field generated by a first linear magnetic field generator provided in a position detecting apparatus.

FIG. 3 is a schematic diagram showing the first linear magnetic field that is generated by the first linear magnetic field generator 9. As shown in FIG. 3, the coil constituting the first linear magnetic field generator 9 is structured so as to hold the torso portion of the subject 1 inside, and to extend in the direction of the z-axis of the reference coordinate axes. Therefore, the first linear magnetic field generated inside the subject 1 by the first linear magnetic field generator 9 has a magnetic field line that travels in the direction of the z-axis of the reference coordinate axes.

The second linear magnetic field generator 10 is to generate the second linear magnetic field that is a linear magnetic field traveling in a direction different from that of the first linear magnetic field. Moreover, the diffuse magnetic field generator 11 is to generate a diffuse magnetic field of which a magnetic field direction is position dependent, the diffuse magnetic field that diffuses as the magnetic field shifts away from the diffuse magnetic field generator 11 in the first embodiment, unlike the first linear magnetic field generator 9 and the second linear magnetic field generator 10.

Figure 4:
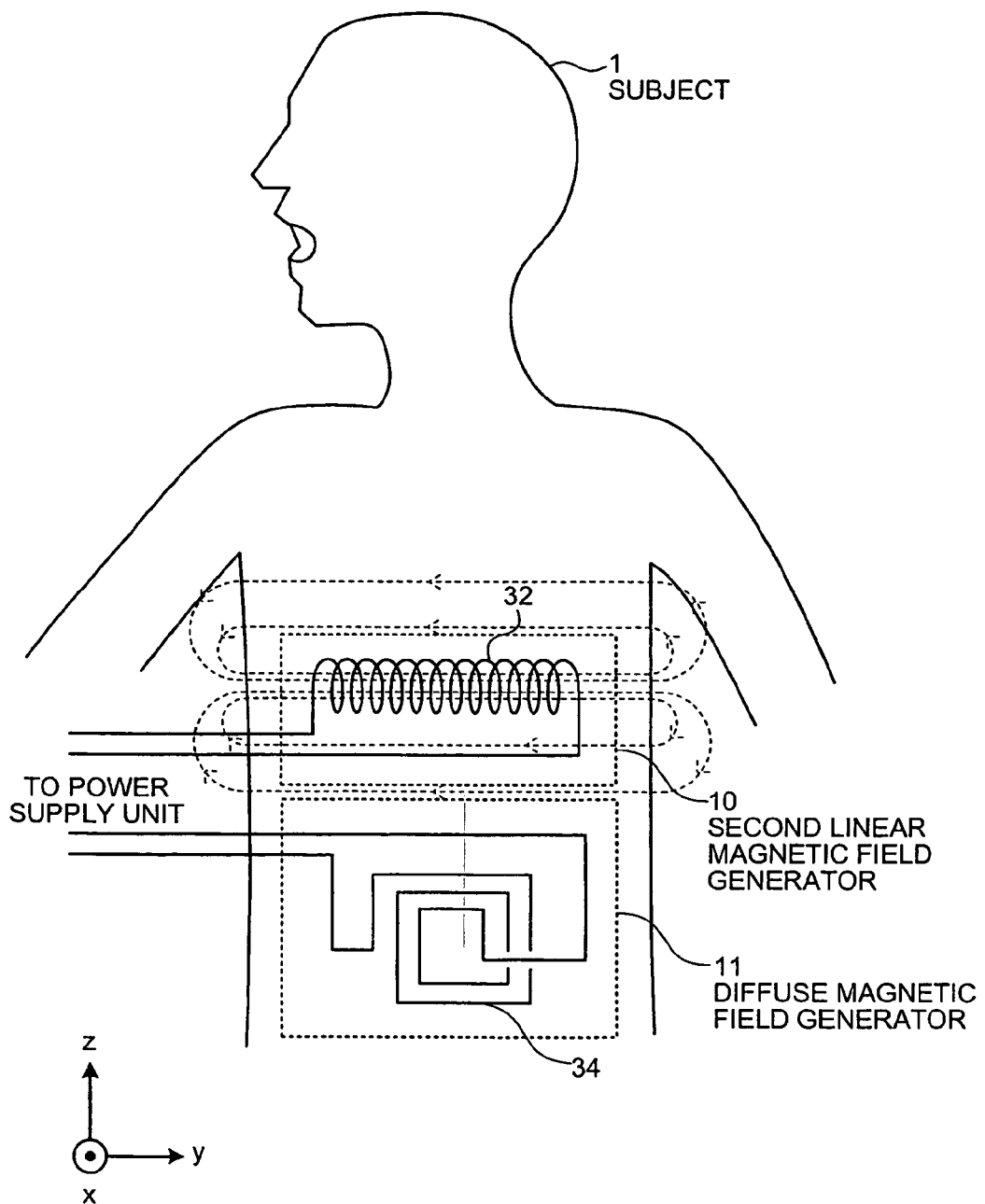
FIG. 4 is a schematic diagram showing configurations of a second linear magnetic field generator and a diffuse magnetic field generator provided in the position detecting apparatus, and showing a mode of a second linear magnetic field generated by the second linear magnetic field generator.

FIG. 4 is a schematic diagram showing configurations of the second linear magnetic field generator 10 and the diffuse magnetic field generator 11, and showing a mode of the second linear magnetic field generated by the second linear magnetic field generator 10. As shown in FIG. 4, the second linear magnetic field generator 10 includes a coil 32 that is formed to extend in a direction of the y-axis of the reference coordinate axes and to have a coil cross-section parallel to an xz plane. Therefore, the second linear magnetic field generated by this coil 32 has a property of being a linear magnetic field at least inside the subject 1 and having the strength that gradually decreases as shifting away from the coil 32, in other words, the strength that is position dependent.

Moreover, the diffuse magnetic field generator 11 includes a coil 34. The coil 32 is arranged so as to generate a magnetic field having a traveling direction in a predetermined direction, and in the first embodiment, it is arranged such that the traveling direction of the linear magnetic field generated by the coil 32 is in the direction of the y-axis of the reference coordinate axes. Furthermore, the coil 34 is fixed at a position at which a diffuse magnetic field is formed that is identical to a magnetic field direction stored in a magnetic-field line orientation database 42 described later.

Figure 5:
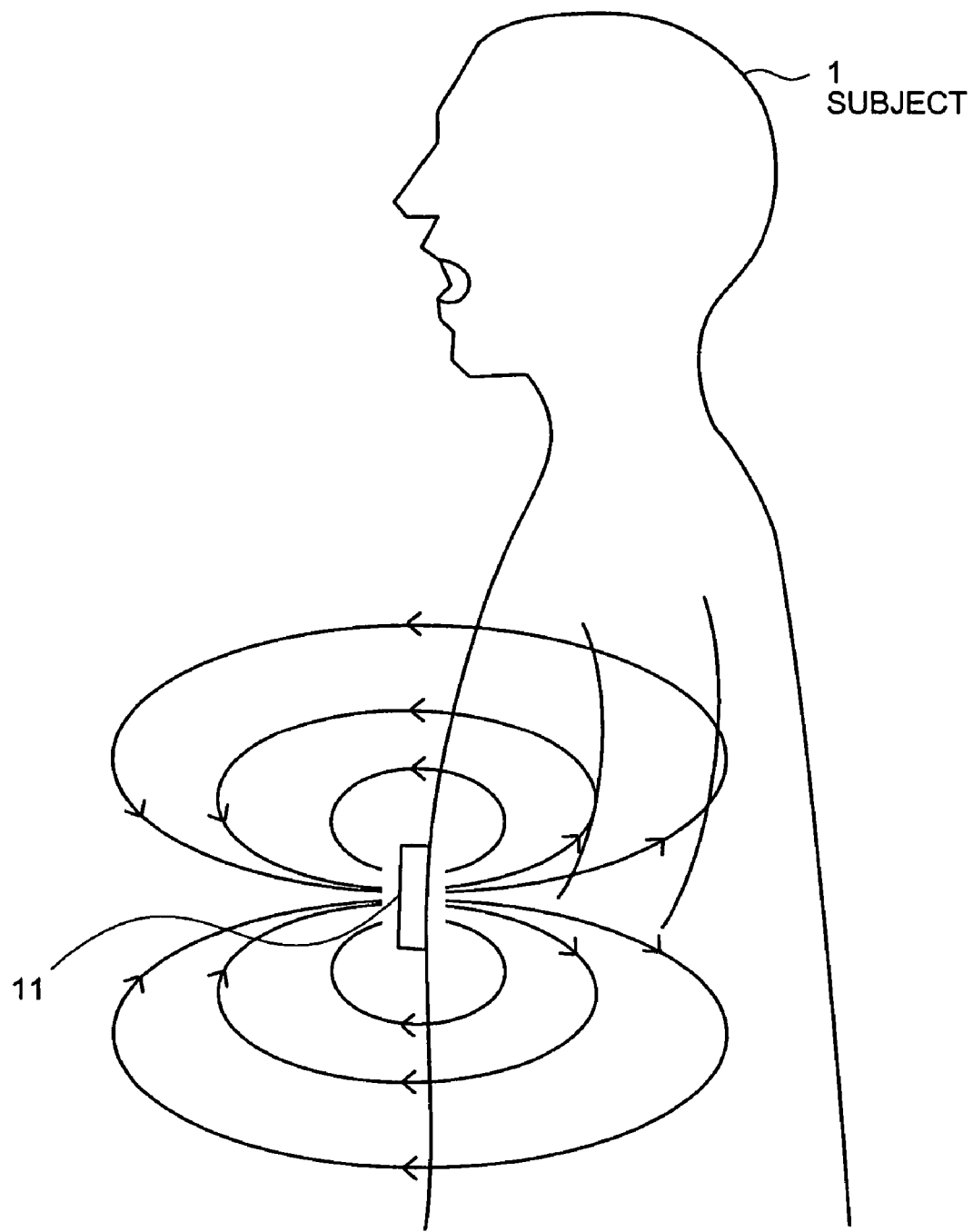
FIG. 5 is a schematic diagram showing a mode of a diffuse magnetic field generated by the diffuse magnetic field generator.

FIG. 5 is a schematic diagram showing a mode of the diffuse magnetic field generated by the diffuse magnetic field generator 11. As shown in FIG. 5, the coil 34 provided in the diffuse magnetic field generator 11 is formed spirally on a surface of the subject 1, and the diffuse magnetic field generated by the diffuse magnetic field generator 11 is generated such that the magnetic field line once radially diffuses and inputs into the coil 34 again in the magnetic field generated by the coil 34 (not shown in FIG. 5) as shown in FIG. 5. Moreover, the diffuse magnetic field generator 11 is also arranged outside the subject 1 and generates a magnetic field radially. Therefore, the diffuse magnetic field generated has such a property that the strength thereof decreases as being away from the coil 34.

The magnetic field sensor 13 will be explained next. The magnetic field sensor 13 is to detect the magnetic field strength of the first linear magnetic field and the like at a predetermined position on an outer surface as one example of body-size information corresponding to an outer surface shape of the subject 1 that differs according to an individual difference, and functions as an example of the body-size information detector of the present invention. The magnetic field sensor 13 is arranged at a predetermined position on the outer surface of the subject 1, for example, at a base of a leg, an abdominal region, a flank, a base of the neck, and the like, and detects the strength of a magnetic field for position detection such as the first linear magnetic field at the arranged position.

It is preferable to arrange the magnetic field sensor 13 such that a distance to a magnetic field generator (for example, the second linear magnetic field 10) is larger than a maximum value of a distance between the area in which the capsule endoscope 2, which is the detection subject at the time of position detection, is possible to be positioned (a possible location area described later in FIG. 8) and the magnetic field generator. Moreover, as a specific configuration of the magnetic field sensor 13, the magnetic field sensor 13 includes an MI sensor and the like similarly to the magnetic field sensor 16 provided in the capsule endoscope 2, and has a function of outputting information on the detected magnetic field strength to the processing device 12.

Figure 6:
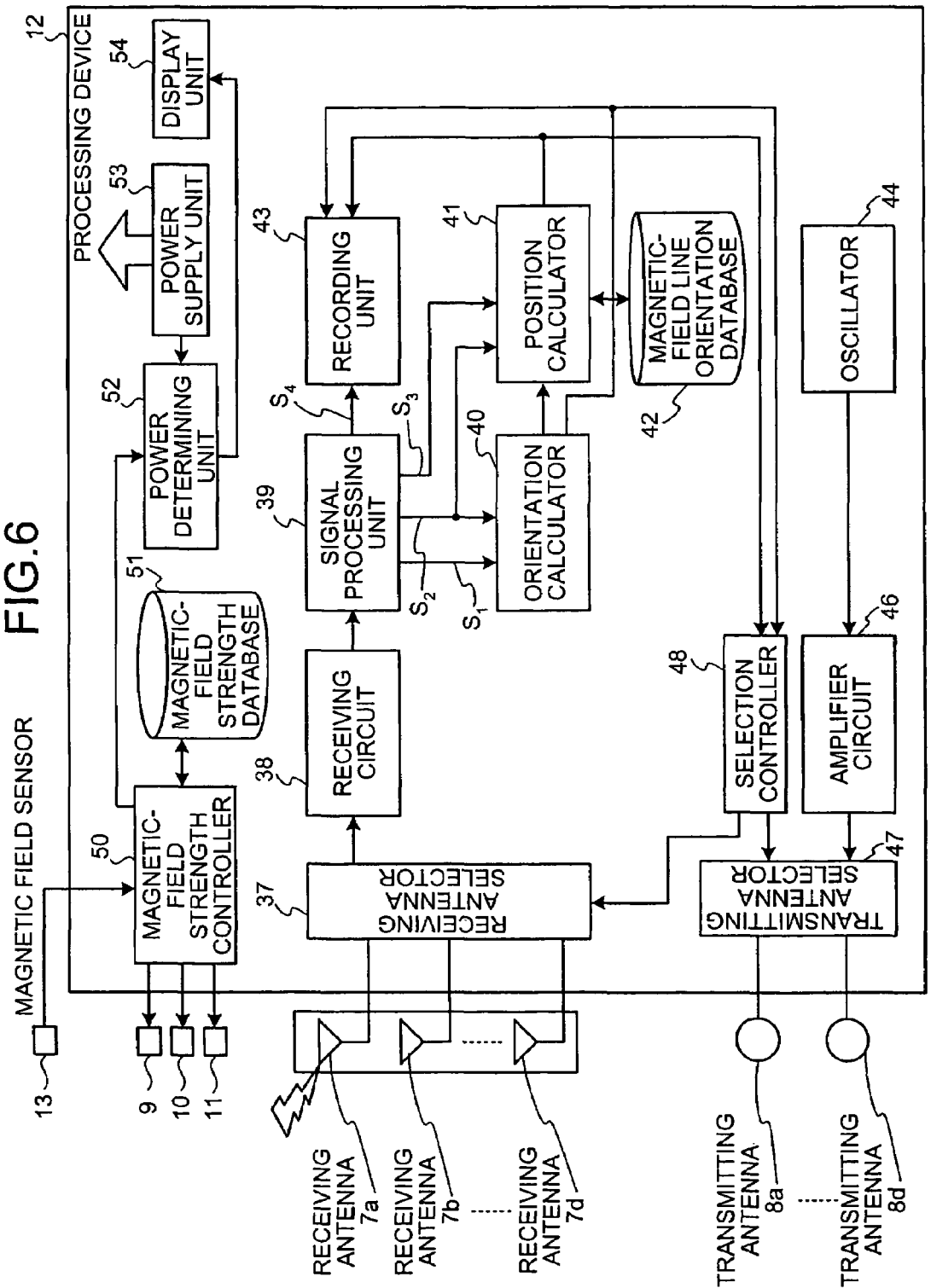
FIG. 6 is a schematic block diagram showing a configuration of a processing device provided in the position detecting apparatus.

The processing device 12 will be explained next. FIG. 6 is a block diagram schematically showing a specific configuration of the processing device 12. First, the processing device 12 has a function of performing a receiving process on a radio signal that is transmitted by the capsule endoscope 2, and corresponding to the function, includes a receiving antenna selector 37 that selects either one of the receiving antennas 7a to 7d, a receiving circuit 38 that extracts an original signal included in the radio signal by performing a demodulation process and the like on the received radio signal, and a signal processing unit 39 that reconstructs an image signal and the like by processing the extracted original signal.

Specifically, the signal processing unit 39 has functions of reconstructing magnetic field signals $S_1$ to $S_3$ and an image signal $S_4$ based on the extracted original signal to output to appropriate components respectively. The magnetic signals $S_1$ to $S_3$ are magnetic field signals corresponding to the first linear magnetic field, the second linear magnetic field, and the diffuse magnetic field respectively detected by the magnetic field sensor 16. Furthermore, the image signal $S_4$ corresponds to an image inside the subject acquired by the in-vivo information acquiring unit 14. As to a specific form of the magnetic field signals $S_1$ to $S_3$, the magnetic field signals $S_1$ to $S_3$ are expressed in a directional vector corresponding to the detected magnetic field strength in the target coordinate axes that are fixed to the capsule endoscope 2, and include information on the magnetic field traveling direction in the target coordinate axes and on the magnetic field strength. The image signal $S_4$ is output to a recording unit 43. The recording unit 43 is to output data to the portable recording medium 5 and has a function of recording a result of position detection and the like described later in the portable recording medium 5, in addition to the image signal $S_4$.

Moreover, the processing device 12 has functions of detecting a position of the capsule endoscope 2 inside the subject 1 based on the magnetic field strength and the like detected by the capsule endoscope 2, and of detecting a orientation indicated by the target coordinate axes fixed to the capsule endoscope 2 with respect to the reference coordinate axes fixed to the subject 1. Specifically, the processing device 12 includes an orientation calculator 40 that calculates the orientation indicated by the target coordinate axes with respective to the reference coordinate axes based on the magnetic field signals $S_1$ and $S_2$ corresponding to the detected strengths of the first linear magnetic field and the second linear magnetic field among signals output by the signal processing unit 39, a position calculator 41 that calculates a position of the capsule endoscope 2 based on the magnetic field signals $S_3$ corresponding to the detected strength of the diffuse magnetic field, the magnetic field signal $S_2$, and a result of calculation by the orientation calculator 40, and the magnetic-field line orientation database 42 that stores correlation between the traveling direction and the position of the magnetic field line that forms the diffuse magnetic field. The orientation calculation and the position calculation by these components will be explained in detail later.

Furthermore, the processing device 12 has a function of transmitting a driving power by radio communication to the capsule endoscope 2, and includes an oscillator 44 that provides a frequency of the radio signal to be transmitted, an amplifier circuit 46 that amplifies the intensity of the radio signal output from the oscillator 44, and a transmitting antenna selector 47 that selects a transmitting antenna to be used for transmission of the radio signal. The radio signal is received by the receiving antenna 28 provided in the capsule endoscope 2, and functions as the driving power of the capsule endoscope 2.

Moreover, the processing device 12 includes a selection controller 48 that controls a mode of the antenna selection by the receiving antenna selector 37 and the transmitting antenna selector 47. The selection controller 48 has a function of selecting the transmitting antenna 8 and the receiving antenna 7 that are most suitable for communication with the capsule endoscope 2, based on the orientation and the position of the capsule endoscope 2 that are calculated by the orientation calculator 40 and the position calculator 41 respectively.

Furthermore, the processing device 12 has a function of controlling the first linear magnetic field generator 9, the second linear magnetic field generator 10, and the diffuse magnetic field generator 11 to generate the magnetic fields having sufficient strength to perform the position detection at such timing before introduction of the capsule endoscope 2 into the subject 1 and the like. Specifically, the processing device 12 includes a magnetic-field strength controller 50 that controls, based on the magnetic field strength detected by the magnetic field sensor 13, strength of the magnetic field generated by the first linear magnetic field generator 9 and the like, and a magnetic-field strength database 51 that stores information necessary at the time of control by the magnetic-field strength controller 50.

The magnetic-field strength controller 50 has a function of performing a control to optimize the strength of the generated magnetic fields on the first linear magnetic field generator 9, the second linear magnetic field generator 10, and the diffuse magnetic field generator 11. Specifically, the magnetic-field strength controller 50 has a function of controlling the strength of the generated magnetic field by controlling power to be supplied to the first linear magnetic field generator 9 and the like to change an amount of a current flowing through the coil provided in the first linear magnetic field generator 9 and the like.

The magnetic-field strength database 51 stores the information necessary at the time of a control operation by the magnetic-field strength controller 50. Specifically, the magnetic-field strength database 51 has a function of storing a permissible range of the magnetic field strength at the position of the magnetic field sensor 13 for each of, for example, the first linear magnetic field generator 9, the second linear magnetic field generator 10, and the diffuse magnetic field generator 11. Specifically, in the first embodiment, a minimum permissible value and a maximum permissible value of the magnetic field strength that is detected by the magnetic field sensor 13 are stored. Based on such information, the magnetic-field strength controller 50 performs a control to change the power to be supplied to the first linear magnetic field generator 9 and the like when it is determined that a result of detection by the magnetic field sensor 13 is actually not within the permissible range.

Furthermore, the processing device 12 includes a power supply unit 53 that is to supply an electric current necessary for the magnetic field generation by the first linear magnetic field generator 9 and the like, and that is attachable and detachable to a main unit of the processing device 12, and has a function of determining whether the power supply unit 53 is capable of supplying sufficient power to the first linear magnetic field generator 9 and the like. Specifically, the processing device 12 includes a power determining unit 52 that determines whether the power supply unit 53 retains necessary power that is acquired based on the control by the magnetic-field strength controller 50, and a display unit 54 to display a result of determination by the power determining unit 52.

An operation of the body-insertable apparatus system according to the first embodiment will be explained next. In the body-insertable apparatus system according to the first embodiment, before performing the position detection, the body-size information of the subject 1 is acquired, the magnetic field strength is controlled based on the body-size information, and power determination to determine whether sufficient power to obtain the controlled magnetic field strength is retained by the power supply unit 53 is performed. Thus, in the following explanation, after an explanation of a magnetic-field strength control operation and a power determining operation, a position detecting operation utilizing the first linear magnetic field and the like is explained. Among the following explanations, an explanation for the magnetic-field strength control operation and the power determining operation is given of a case of the second linear magnetic field as an example, however, in an actual operation in the body-insertable apparatus system, a similar control operation is executed also in a case of the first linear magnetic field and the diffuse magnetic field.

Figure 7:
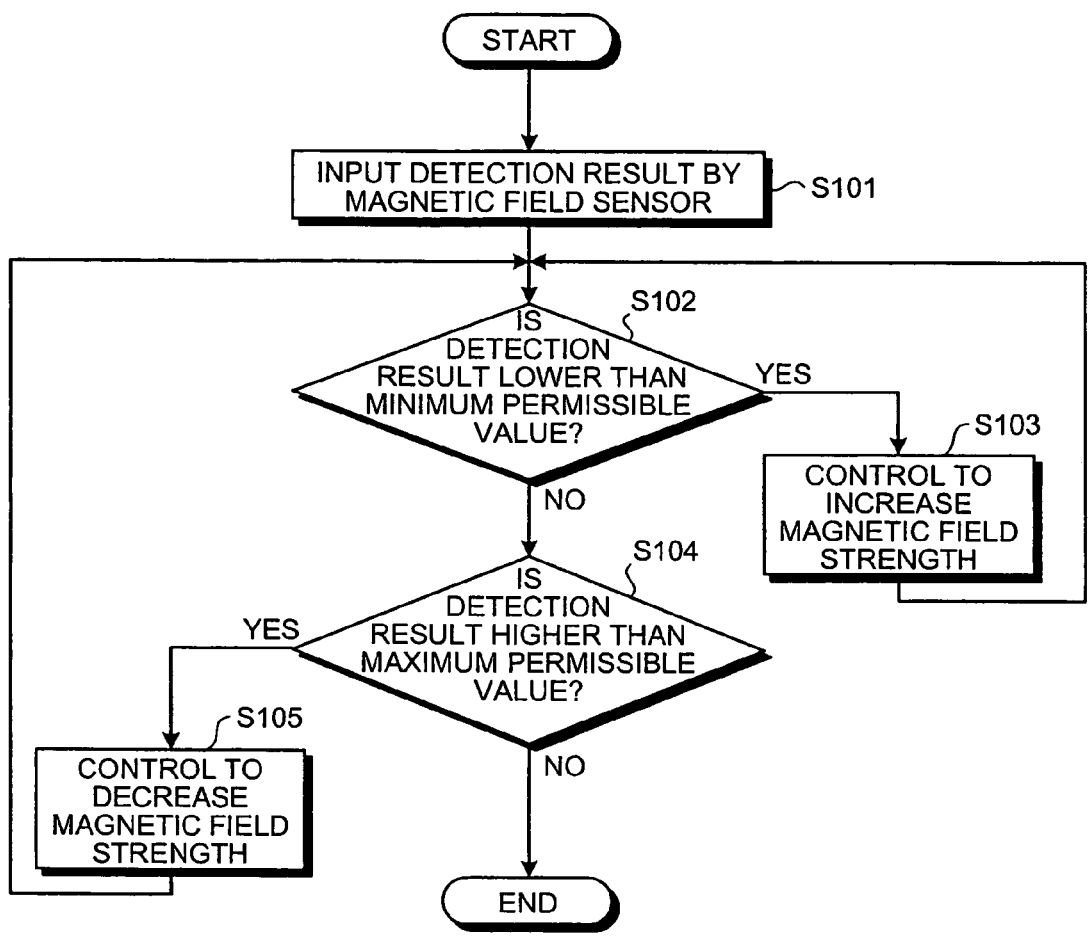
FIG. 7 is a flowchart for explaining contents of a process performed by a magnetic-field strength controller.

FIG. 7 is a flowchart showing the control operation performed by the magnetic-field strength controller 50 in the body-insertable apparatus system according to the first embodiment. As shown in FIG. 7, the magnetic-field strength controller 50 first inputs the magnetic field strength of the second linear magnetic field detected by the magnetic field sensor 13 that is arranged at a predetermined position on the outer surface of the subject 1 as the body-size information (step S101). It is determined whether a value of the magnetic field strength of the detection result is lower than the minimum permissible value recorded in the magnetic-field strength database 51 (step S102). When the magnetic field strength is lower than the minimum permissible value (step S102: Yes), the magnetic-field strength controller 50 controls the second linear magnetic field generator 10 to increase the strength of the second linear magnetic field (step S103), and the process returns to step S102 to repeat the above process. On the other hand, when the magnetic field strength is equal to or higher than the minimum permissible value (step S102: No), it is further determined whether the value of the magnetic field strength of the detection result is higher than the maximum permissible value recorded in the magnetic-field strength database 51 (step S104). When the value of the magnetic field strength is higher than the maximum permissible value, the magnetic-field strength controller 50 controls the second linear magnetic field generator 10 to decrease the strength of the second linear magnetic field (step S105), and the process returns to step S102 to repeat the above process. By repeating the above process, the strength of the second linear magnetic field at the position at which the magnetic field sensor 13 is arranged converges to a value between the minimum permissible value and the maximum permissible value recorded in the magnetic-field strength database 51. Thus, a similar control process is performed on the first magnetic field generator 9 that generates the first magnetic field and the diffuse magnetic field generator 11 that generates the diffuse magnetic field so that the magnetic fields respectively generated are also controlled to have the strength falling between a predetermined minimum permissible value and a maximum permissible value at the position at which the magnetic field sensor 13 is arranged.

Figure 8:
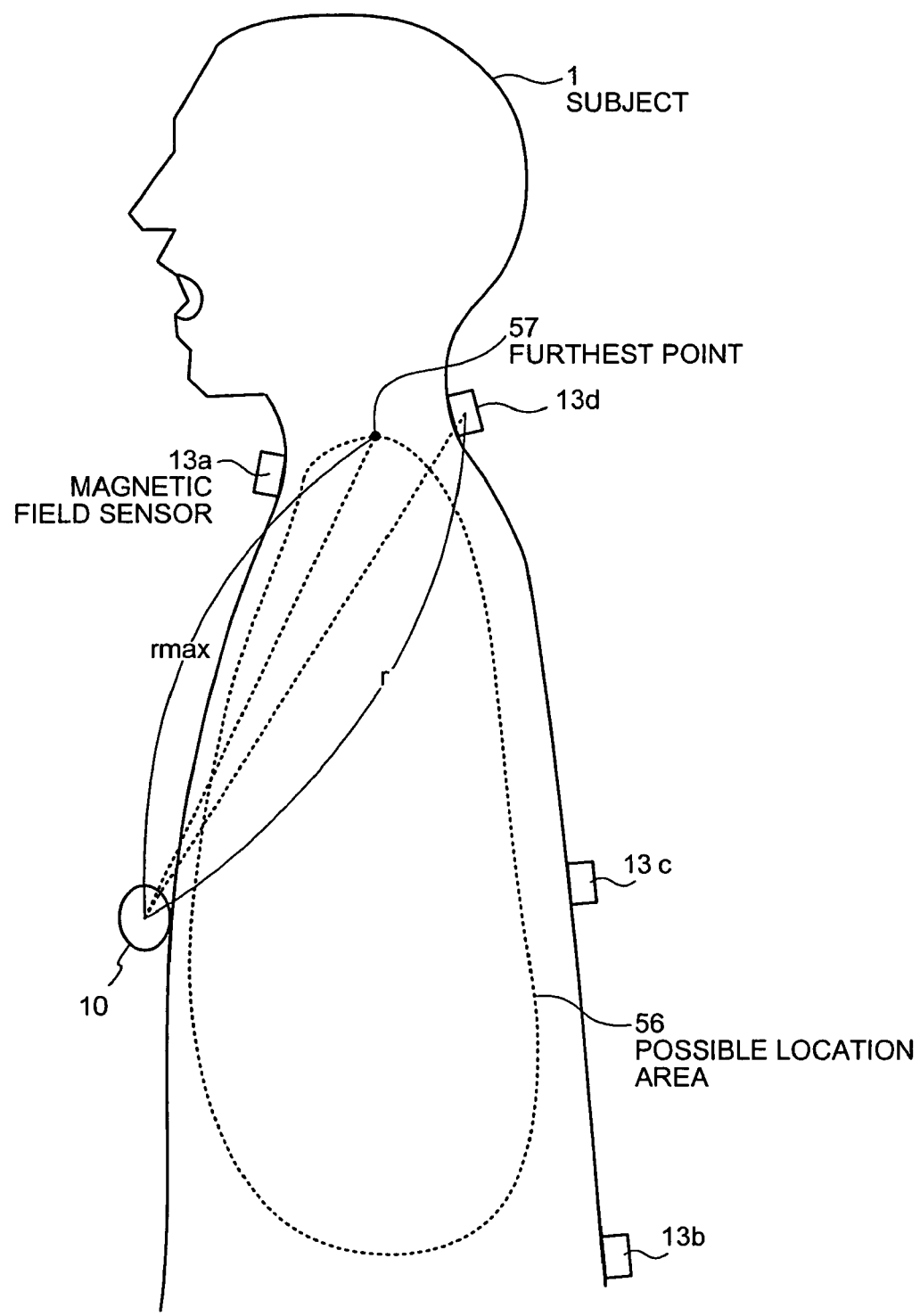
FIG. 8 is a schematic diagram showing contents of the process performed by the magnetic-field strength controller.

The meaning of the magnetic-field strength control process will be briefly explained. FIG. 8 is a schematic diagram showing the second linear magnetic field generated by the second linear magnetic field generator 10 as a result of the magnetic field strength control. As shown in FIG. 8, a plurality of magnetic field sensors 13a to 13d are respectively arranged on the outer surface of the subject 1, and among these sensors, the magnetic field sensor 13d is arranged at a position having a distance to the second linear magnetic field generator 10 being larger than a maximum value of a distance between a possible location area 56 that is the area in which the capsule endoscope 2 can be located and the second linear magnetic field generator 10. Specifically, as shown in FIG. 8, the magnetic field sensor 13d is arranged such that a value of a distance r to the second linear magnetic field generator 10 is larger than a distance $r_{max}$ between a furthest point 57 that is the furthest position from the second linear magnetic field generator 10 on the border of the possible location area 56 and the second linear magnetic field generator 10.

A case is considered in which the magnetic field strength detected by the magnetic field sensor 13d in such a configuration is used as the body-size information, and in which the value of the magnetic field strength detected by the magnetic field sensor 13d is maintained between the minimum permissible value and the maximum permissible value. Generally, the magnetic field generated by the magnetic field generator does not increase the strength thereof as being away from the magnetic field generator, and in the case of the second linear magnetic field generated by the second linear magnetic field generator 10, the strength thereof gradually decreases as being away from the second linear magnetic field generator 10. Therefore, at a region in the possible location area 56 closer to the second linear magnetic field generator 10 than the magnetic field sensor 13d, the strength of the second linear magnetic field should have a value equal to or higher than the minimum permissible value at a predetermined position. Moreover, at a position outside the body of the subject 1 located further from the second linear magnetic field generator 10 than the magnetic field sensor 13d, the strength of the second linear magnetic field should have a value equal to or lower than the maximum permissible value. Thus, the magnetic-field strength controller 50 controls the strength of the magnetic field inside and outside the body of the subject 1 by controlling the driving condition of the second linear magnetic field generator 10 using the magnetic field sensor 13d.

Figure 9:
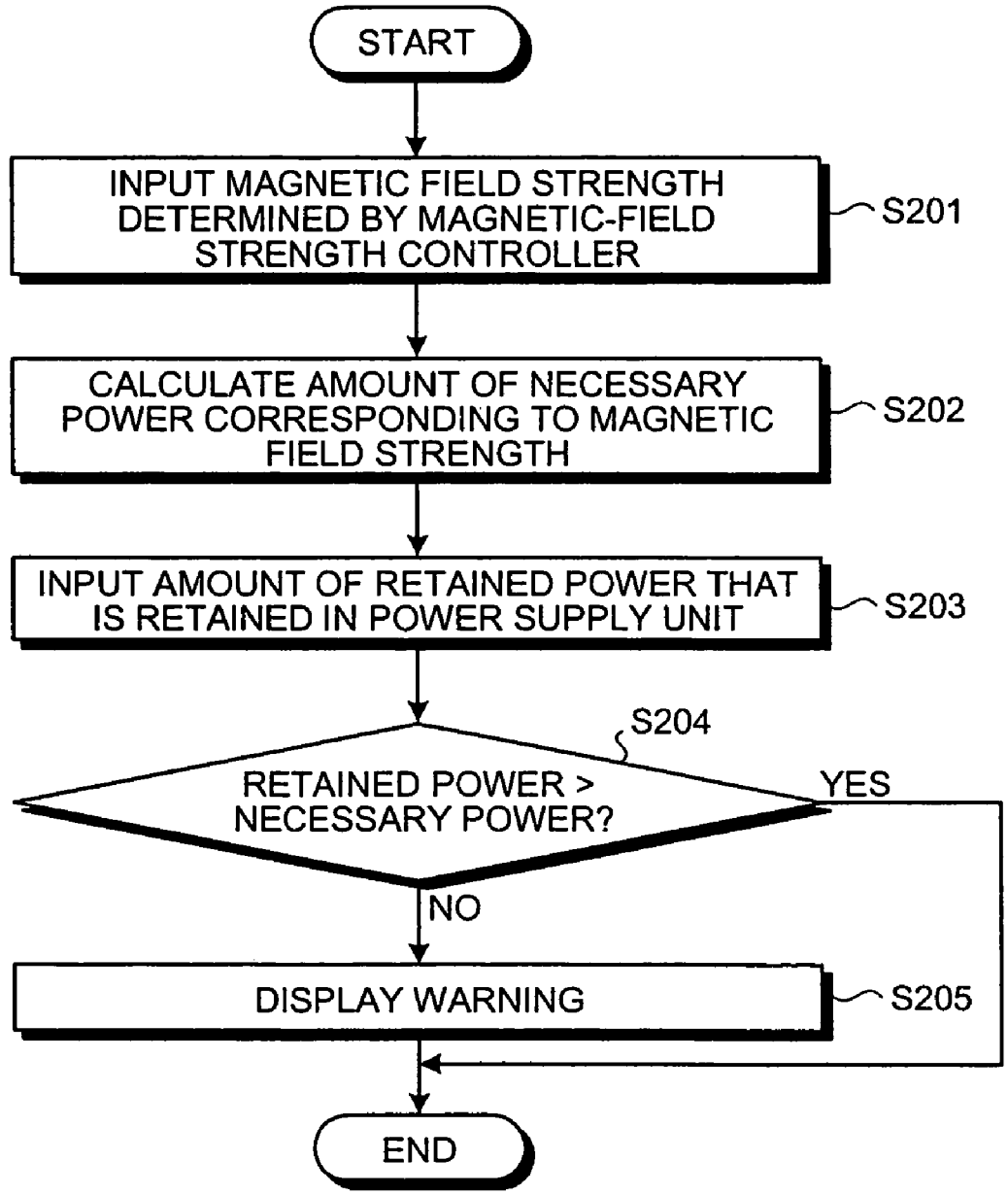
FIG. 9 is a flowchart for explaining contents of a process performed by a power determining unit.

The power determination process by the power determining unit 52 will be explained next. FIG. 9 is a flowchart for explaining a process performed by the power determining unit. As shown in FIG. 9, the power determining unit 52 first acquires a value of the magnetic field strength determined by the magnetic-field strength controller 50 (step S201). If more than one control subject, such as the first linear magnetic field generator 9, the second linear magnetic field generator 10, and the diffuse magnetic field generator 11 as in the first embodiment, is provided, each value of the magnetic field strength calculated for each is input. The power determining unit 52 calculates an amount of power necessary for the first linear magnetic field generator 9 and the like to realize the magnetic field strength of each for a predetermined period of time (step S202), and on the other hand, acquires a value of retained power that indicates an amount of power retained in the power supply unit 53 (step S203). The power determining unit 52 determines whether the amount of the retained power acquired at step S203 is more than the amount of the necessary power calculated at step S202 (step S204). When it is determined that the amount of the retained power is more than the amount of the necessary power (step S204: Yes), the power determination process is finished. On the other hand, when the amount of the necessary power is more than the amount of retained power, a predetermined warning for possibility of shortage of power is displayed for a user (step S205). Note that at step S202, power consumed by components of the processing device 12 is also added. Since a value of such power is not dependent on the individual difference of the subject 1 and is substantially fixed, the value is stored as data by, for example, the power determining unit 52 in advance.

After the above magnetic-field strength control and the power determination process are completed, the capsule endoscope 2 is introduced into the subject 1, and position detection of the capsule endoscope 2 inside the subject 1 is performed while acquiring the in-vivo information. The position detection of the capsule endoscope 2 of the detection subject in the body-insertable apparatus system according to the first embodiment will be explained.

The body-insertable apparatus system according to the first embodiment has a configuration to calculate a positional relationship between the reference coordinate axes that are fixed to the subject 1 and the target coordinate axes that are fixed to the capsule endoscope 2. Specifically, orientation of the target coordinate axes with respect to the reference coordinate axes is calculated, and based on the calculated orientation, a position of an origin of the target coordinate axes in the reference coordinate axes, that is, the position of the capsule endoscope 2 inside the subject 1, is calculated. Therefore, in the following explanation, an orientation calculation mechanism is first explained, and then, a position calculation mechanism based on the calculated orientation is explained, however, the application of the present invention is of course not limited to a system having this position detection mechanism.

Figure 10:
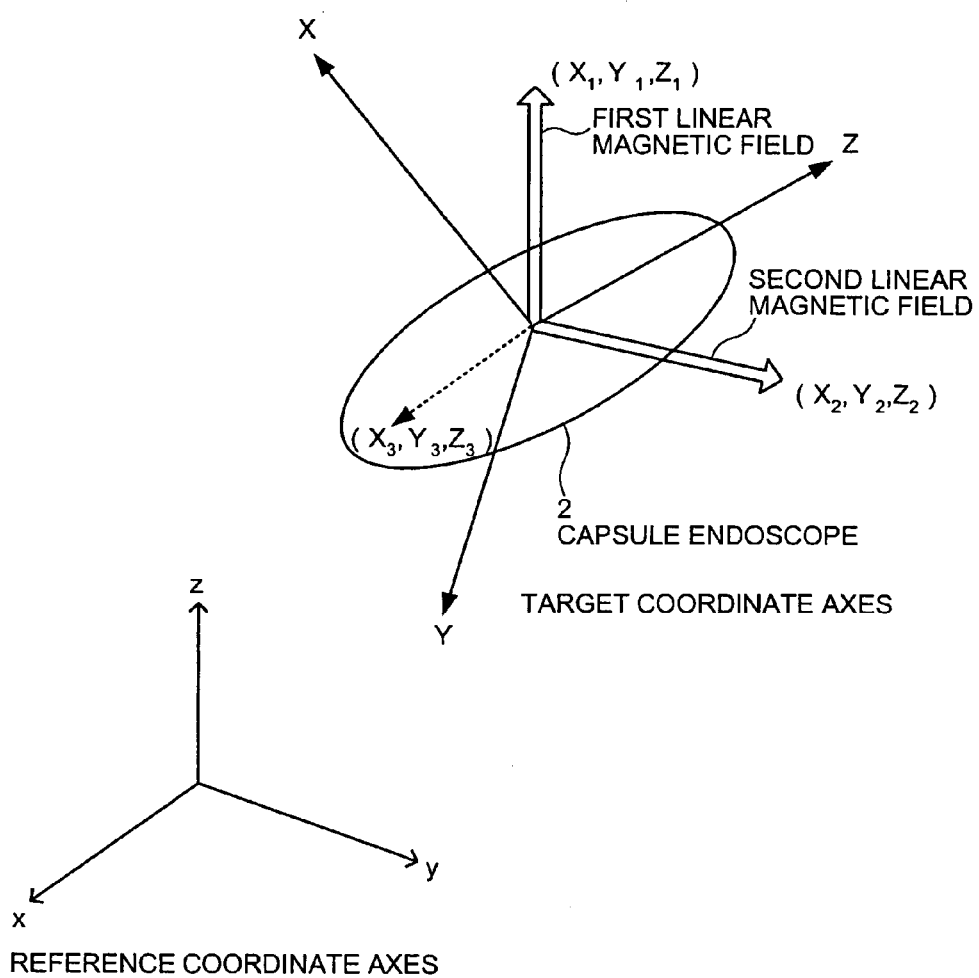
FIG. 10 is a schematic diagram showing a relationship between reference coordinate axes and target coordinate axes.

The orientation calculation mechanism achieved by the orientation calculator 40 will be explained. FIG. 10 is a schematic diagram showing a relationship between the reference coordinate axes and the target coordinate axes when the capsule endoscope 2 is moving inside the subject 1. As described above, the capsule endoscope 2 moves forward along the passing channel, and rotates about a traveling direction as an axis for a predetermined angle. Therefore, the target coordinate axes deviate in orientation as shown in FIG. 10 from the reference coordinate axes.

On the other hand, the first linear magnetic field generator 9 and the second linear magnetic field generator 10 are respectively fixed to the subject 1. Therefore, the first and the second linear magnetic fields generated by the first linear magnetic field generator 9 and the second linear magnetic field generator 10 travel in directions fixed with respect to the reference coordinate axes, specifically, in the direction of the z-axis of the reference coordinate axes for the first magnetic field, and in the direction of the y-axis for the second linear magnetic field in the case when the second linear magnetic field generator 10 is used.

The orientation calculation is executed using the first linear magnetic field and the second magnetic field in the first embodiment. Specifically, traveling directions of the first linear magnetic field and the second magnetic field provide in a time-sharing manner are detected by the magnetic field sensor 16 in the capsule endoscope 2 first. The magnetic field sensor 16 is configured to detect magnetic field components in the directions of the X-axis, the Y-axis, and the Z-axis in the target coordinate axes, and information on the traveling direction in the target coordinate axes of the first linear magnetic field and the second magnetic field detected are transmitted to the position detecting apparatus 3 through the radio transmitting unit 19.

The radio signal transmitted by the capsule endoscope 2 is subjected to processes by the signal processing unit 39 and the like, to be output as the magnetic field signals $S_1$ and $S_2$. For example, in the example shown in FIG. 10, the magnetic field signal $S_1$ includes information on coordinates $(X_1, Y_1, Z_1)$ as the traveling direction of the first linear magnetic field, and the magnetic field signal $S_2$ includes information on coordinates $(X_2, Y_2, Z2)$ as the traveling direction of the second linear magnetic field. Upon input of the magnetic field signals $S_1$ and $S_2$, the orientation calculator 40 calculate the orientation of the target coordinate axes with respect to the reference coordinate axes. Specifically, the orientation calculator 40 understands that coordinates $(X_3, Y_3, Z_3)$ at which a value of the inner product of both $(X_1, Y_1, Z_1)$ and $(X_2, Y_2, Z_2)$ in the target coordinate axes is 0 correspond to the direction of the z-axis in the reference coordinate axes. The orientation calculator 40 performs a predetermined coordinate conversion process based on the above correspondence, and calculates coordinates in the reference coordinate axes that correspond to the X-axis, the Y-axis, and the Z-axis in the target coordinate axes, and output the coordinates as orientation information. This is the orientation calculation mechanism achieved by the orientation calculator 40.

The position detection mechanism of the capsule endoscope 2 achieved by the position calculator 41 based on the calculated orientation information will be explained next. The position calculator 41 has such a configuration that the magnetic field signals $S_2$ and $S_3$ are input from the signal processing unit 39, the orientation information is input from the orientation calculator 40, and information stored in the magnetic-field line orientation database 42. The position calculator 41 performs the position calculation of the capsule endoscope 2 based on the input information as follows.

Figure 11:
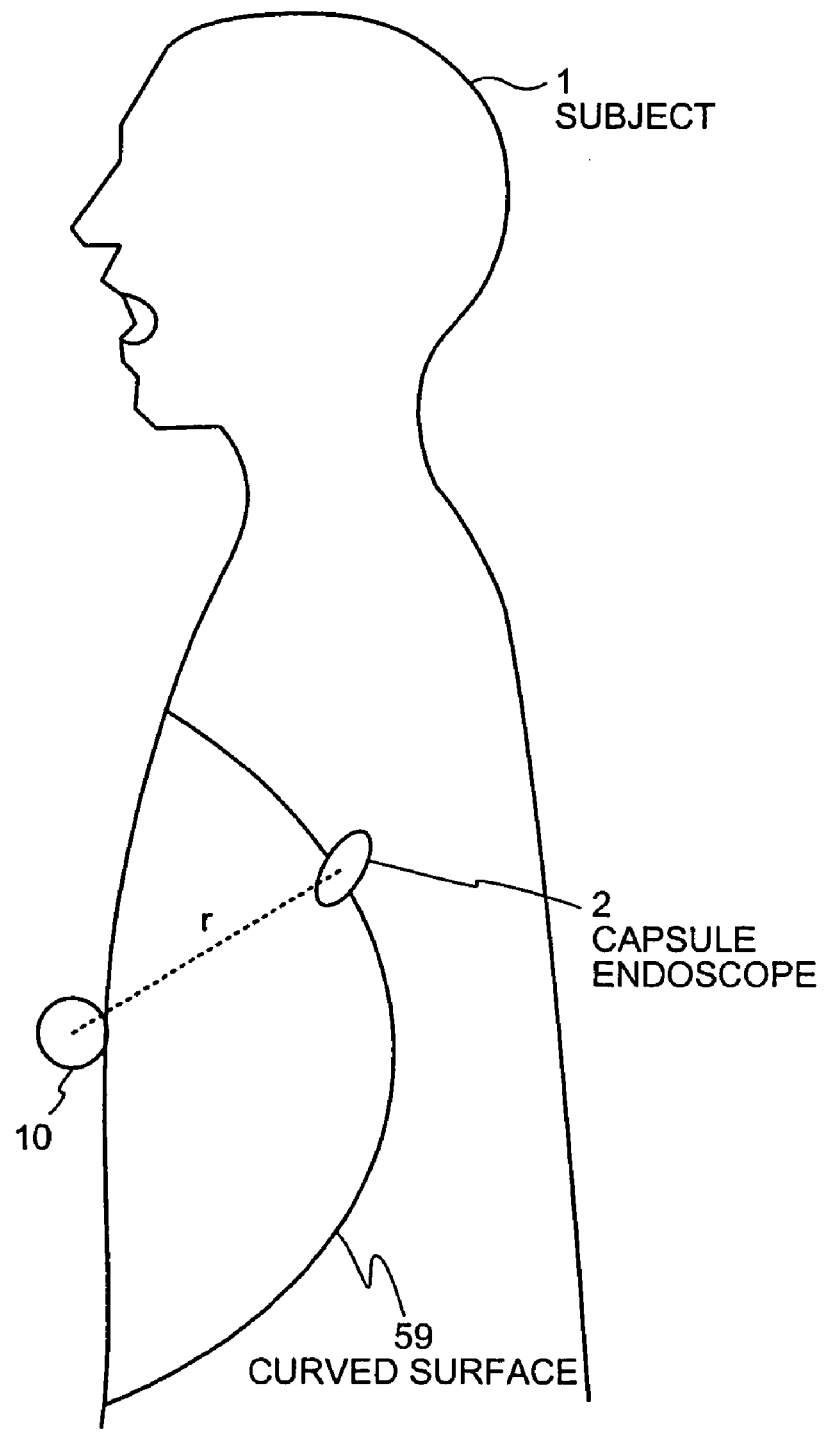
FIG. 11 is a schematic diagram showing an application mode of the second linear magnetic field at the time of position calculation.

The position calculator 41 first calculates a distance between the second linear magnetic field generator 10 and the capsule endoscope 2 based on the magnetic field signal $S_2$. The magnetic field signal $S_2$ corresponds to a result of detection of the second linear magnetic field in the location area of the capsule endoscope 2, and the second linear magnetic field has a property that the strength thereof decreases as being away from the second linear magnetic field generator 10, corresponding to the second linear magnetic field generator 10 being arranged outside the subject 1. The position calculator 41 utilizes the property, and calculates a distance r between the second linear magnetic field and the capsule endoscope 2 by comparing the strength of the second linear magnetic field near the second linear magnetic field generator 10 (acquired based on the current fed to the second linear magnetic field generator 10) and the strength of the second linear magnetic field in the location area of the capsule endoscope 2 acquired based on the magnetic field signal $S_2$. As a result of calculation of the distance r, it is known that the capsule endoscope 2 is positioned on a curved surface 59 that is an assembly of points that are distant for the distance r from the second linear magnetic field generator 10 as shown in FIG. 11.

Figure 12:
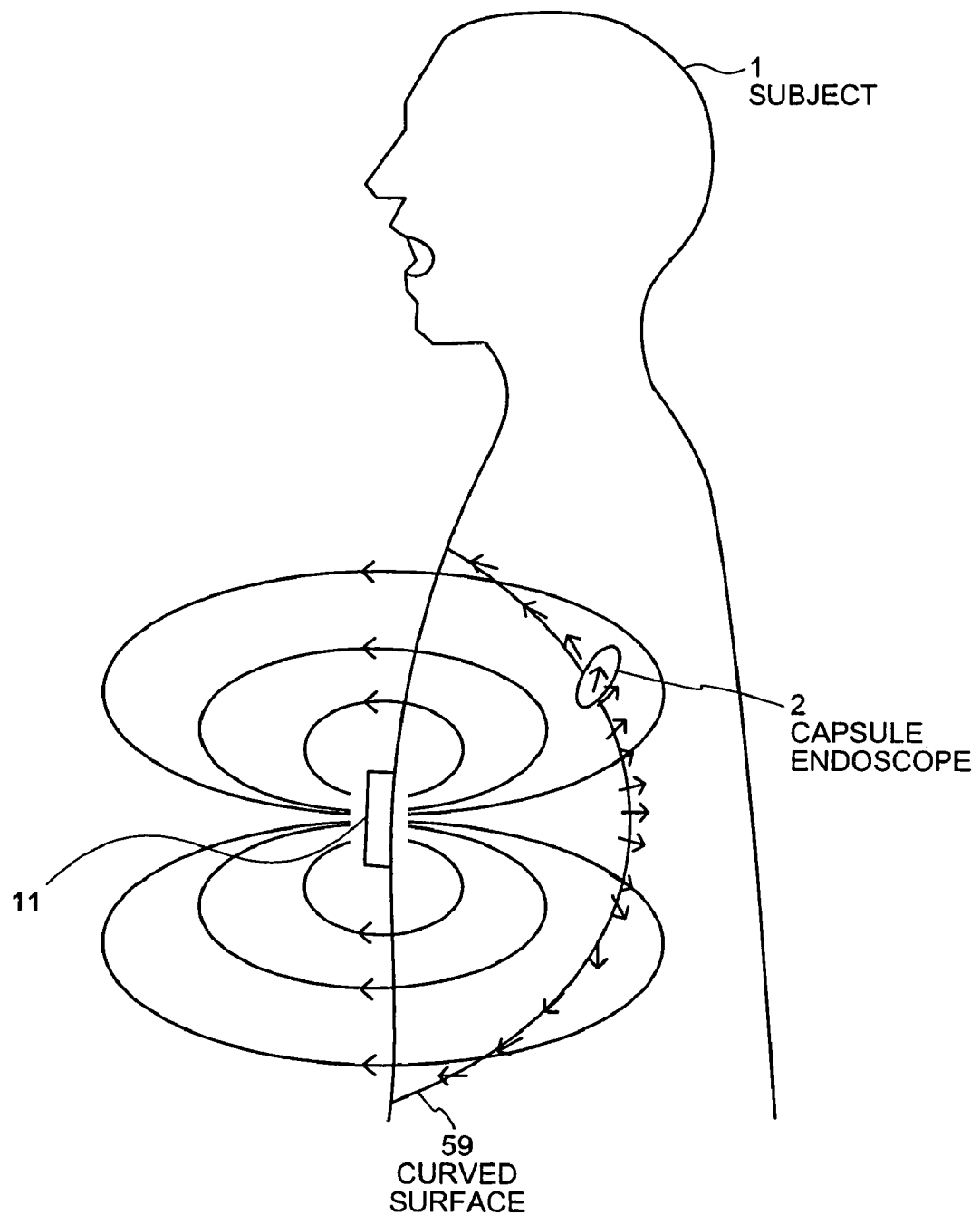
FIG. 12 is a schematic diagram showing an application mode of the diffuse magnetic field at the time of position detection.

The position calculator 41 then calculates a position of the capsule endoscope 2 on the curved surface 59 based on the magnetic field signal $S_3$, the orientation information calculated by the orientation calculator 40, and the information stored in the magnetic-field line orientation database 42. Specifically, the traveling direction of the diffuse magnetic field at the position of the capsule endoscope 2 is calculated based on the magnetic field signal $S_3$ and the orientation information. Since magnetic field signal $S_3$ is a signal corresponding to a result of detection of the diffuse magnetic field based on the reference coordinate axes, the traveling direction of the diffuse magnetic field in the reference coordinate axes at the position of the capsule endoscope 2 is calculated by performing, on the traveling direction of the diffuse magnetic field based on magnetic field signal $S_3$, the coordinate conversion process from the target coordinate axes to the reference coordinate axes based on the orientation information. Since the magnetic-field line orientation database 42 stores correlation between the traveling direction and the position of the diffuse magnetic field in the reference coordinate axes, the position calculator 41 calculates the position corresponding to the calculated traveling direction of the diffuse magnetic field, by referring to the information stored in the magnetic-field line orientation database 42 as shown in FIG. 12, and determines the detected position as the position of the capsule endoscope 2. By performing the above processes, the orientation and the position of the capsule endoscope 2 inside the subject 1 are calculated. Thus, the position detection is completed.

An advantage of the body-insertable apparatus system according to the first embodiment will be explained next. First, the body-insertable apparatus system according to the first embodiment has an advantage of being capable of generating the magnetic field for position detection having sufficient strength at the time of the position detection regardless of a difference in body sizes because of the individual difference of the subject 1. In the first embodiment, the magnetic field sensor 13 is arranged on the outer surface of the subject 1, and the distance between the magnetic field generator (for example, the second linear magnetic field generator 10) and the magnetic field sensor 13 varies according to the body size of the subject 1. Therefore, the magnetic field strength detected by the magnetic field sensor 13 reflects the body size, in other words, functions as the body-size information that corresponds to the shape of the outer surface of the subject 1, and the magnetic field sensor 13 functions as the body-size information detector. In the first embodiment, the magnetic-field strength controller 50 is provided that controls the magnetic field generator to generate the magnetic field having the optimal strength based on the body-size information, and by adjusting, by the magnetic-field strength controller 50, the strength of the magnetic field generated by the magnetic field generator such as the second linear magnetic field generator 10, it is possible to generate the magnetic field having sufficient strength regardless of a difference in body size of the subject 1.

More specifically, in the first embodiment, as shown in FIG. 8, at least one of one or more units of the magnetic field sensor 13 is arranged at such a position that the distance to the magnetic field generator (for example, the second linear magnetic field generator 10) is larger than the maximum value of the distance between the possible location area of the capsule endoscope 2, which is the detection subject of the position detection, and the magnetic field generator. General magnetic fields such as the second linear magnetic field never increase the strength thereof with distance, but usually have a property of decreasing with distance, therefore, when the magnetic field sensor 13 is arranged at the above position, a magnetic field having strength higher than the magnetic field strength detected by the magnetic field sensor 13 is generated in all areas inside the possible location area 56. Therefore, as for the magnetic field strength detected by the magnetic field sensor 13, if the minimum permissible value to be stored in the magnetic-field strength database 51 is appropriately set, for example, to the minimum strength that can be detected by the magnetic field sensor 16 provided in the capsule endoscope 2, the magnetic field for position detection can be detected by the magnetic field sensor 16 in the capsule endoscope 2 in all areas inside the possible location area 56 regardless of the difference in body sizes.

Moreover, in the first embodiment, it is possible to reduce influence of the magnetic field for position detection to other electronic devices outside the subject 1. As described above, general magnetic fields such as the magnetic field for position detection never increase the strength with distance from the magnetic field generator, but usually decrease, therefore, the magnetic field strength at an area located further than the magnetic field sensor 13 to the magnetic field generator takes a value equal to or lower than a value detected by the magnetic field sensor 13. Therefore, by appropriately setting the value of the maximum permissible value to be stored in the magnetic-field strength database 51, it is possible to suppress the strength of the magnetic field generated by the magnetic field generator at the outside of the subject 1, thereby reducing the influence to the electronic devices and the like around the subject 1.

Furthermore, in the first embodiment, it is configured to control the magnetic field strength by adjusting power to be supplied by the magnetic-field strength controller 50, and the power determining unit 52 is provided that determines whether the power supply unit 53 can supply the power to be supplied that is calculated by the magnetic-field strength controller 50. In other words, the body-insertable apparatus according to the present embodiment adopts such a configuration that the magnetic-field strength controller 50 changes the amount of power supplied to the magnetic field generator to generate a magnetic field having strength that is necessary and sufficient at the time of detection according to the individual difference of the subject 1. Therefore, such a mechanism is required that determines whether the retained power that is retained in the power supply unit 53 is sufficient for the necessary power that varies, and in the present embodiment, the power determining unit 52 that performs such determination is additionally provided. The power determining unit 52 provides an advantage of being possible to grasp such a problem in advance that the amount of the retained power in the power supply unit 53 is insufficient, for example, when the subject 1 is a big adult male, and to take measures such as exchange to a large capacity one of the power supply unit 53 in advance.

Second Embodiment

A body-insertable apparatus system according to a second embodiment will be explained next. The body-insertable apparatus system according to the second embodiment has a function of performing position detection using earth magnetism instead of the magnetic field generated by the first linear magnetic field generator as the first linear magnetic field.

Figure 13:
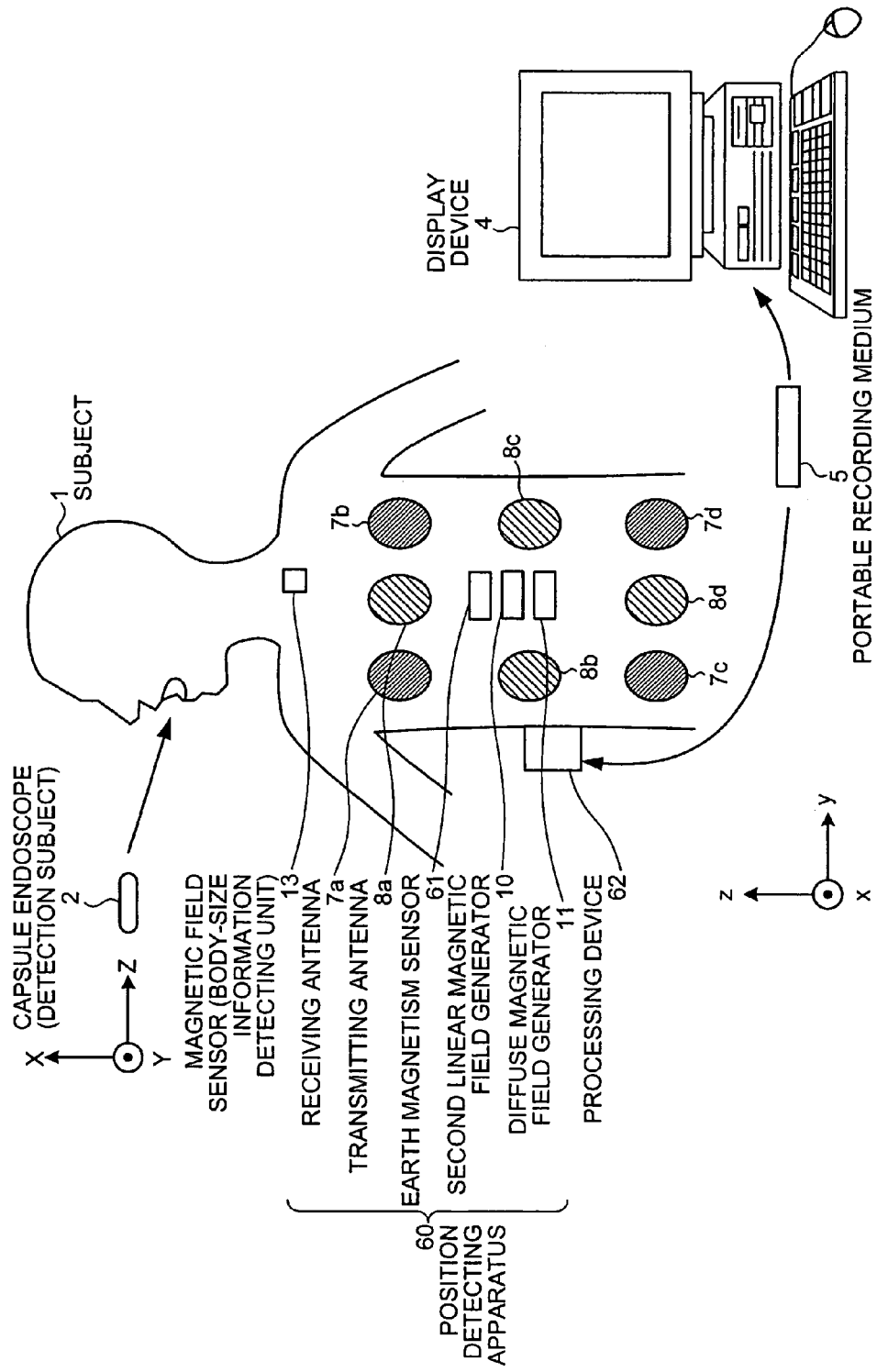
FIG. 13 is a schematic diagram showing an entire configuration of a body-insertable apparatus system according to a second embodiment of the present invention.

FIG. 13 is a schematic diagram showing an entire configuration of the body-insertable apparatus system according to the second embodiment. As shown in FIG. 13, while the body-insertable apparatus system according to the second embodiment includes the capsule endoscope 2, the display device 4, and the portable recording medium 5 similarly to the first embodiment, a position detecting apparatus 60 has a different configuration. Specifically, the first linear magnetic field generator 9 provided in the position detecting apparatus in the first embodiment is omitted, and an earth magnetism sensor 61 is newly provided. Moreover, a processing device 62 has a different configuration from the first embodiment and the like.

The earth magnetism sensor 61 basically has the same configuration as the magnetic field sensor 16 provided in the capsule endoscope 2. Specifically, the earth magnetism sensor 61 has functions of detecting strength of the magnetic field components in predetermined three axial directions at an arranged area, and of outputting an electrical signal corresponding to the detected magnetic field strength. On the other hand, the earth magnetism sensor 61 is arranged on the outer surface of the subject 1 unlike the magnetic field sensor 16, and has a function of detecting the strength of the magnetic field components corresponding to the directions of the x-axis, the y-axis, and the z-axis in the reference coordinate axes fixed to the subject 1 respectively. In other words, the earth magnetism sensor 61 has a function of detecting a traveling direction of the earth magnetism, and of outputting the electrical signal corresponding to the magnetic field strength detected in the directions of the x-axis, the y-axis, and the z-axis, to the processing device 62.

Figure 14:
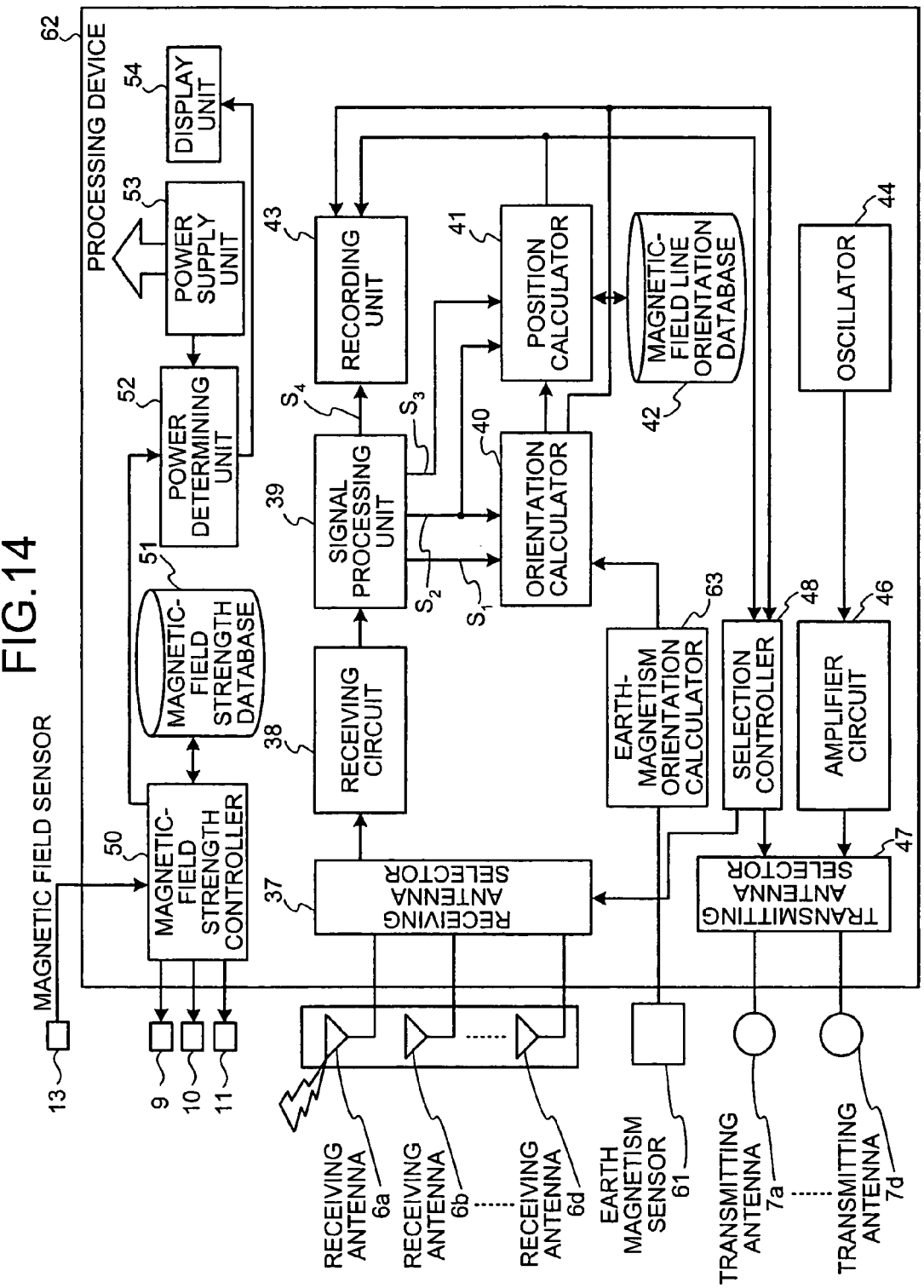
FIG. 14 is a schematic block diagram showing a configuration of a processing device provided in the position detecting apparatus.

The processing device 62 according to the second embodiment will be explained next. FIG. 14 is a block diagram showing a configuration of the processing device 62. As shown in FIG. 14, the processing device 62 basically has a similar configuration as the processing device 12 of the first embodiment, but has a configuration in which an earth-magnetism orientation calculator 63 is provided that calculates the traveling direction of the earth magnetism in the reference coordinate axes based on the electrical signal input from the earth magnetism sensor 61, and that outputs a result of calculation to the orientation calculator 40.

The problem in the case of using the earth magnetism as the first linear magnetic field is calculation of the traveling direction of the earth magnetism on the reference coordinate axes that are fixed to the subject 1. Specifically, since the subject 1 can freely move even while the capsule endoscope 2 is moving inside the body of the subject 1, a positional relationship between the reference coordinate axes fixed to the subject 1 and the earth magnetism is expected to change according to movement of the subject 1. In terms of calculation of the positional relation of the target coordinate axes with respect to the reference coordinate axes, there is a problem in that if the traveling direction of the first linear magnetic field is unidentified, the correlation between the reference coordinate axes and the target coordinate axes with respect to the traveling direction of the first linear magnetic field cannot be identified.

Therefore, in the second embodiment, the earth magnetism sensor 61 and the earth-magnetism orientation calculator 63 are provided to monitor the traveling direction of the earth magnetism that changes on the reference coordinate axes due to the movement and the like of the subject 1. Specifically, the earth-magnetism orientation calculator 63 calculates the traveling direction of the earth magnetism on the reference coordinate axes based on a result of detection by the earth magnetism sensor 61, and outputs a result of calculation to the orientation calculator 40. On the other hand, the orientation calculator 40 calculates correlation between the reference coordinate axes and the target coordinate axes for the traveling direction of the earth magnetism based on the input traveling direction of the earth magnetism, thereby calculating the orientation information together with the correlation for the second linear magnetic field.

Depending on orientation of the subject 1, the traveling direction of the earth magnetism and the second linear magnetic field generated by the second linear magnetic field generator 10 become parallel with each other. In such a case, it is possible to detect the positional relation by additionally using data on the orientation of the target coordinate axes at a time immediately before and the position of the origin. Moreover, to prevent the earth magnetism and the second linear magnetic field from being parallel with each other, it is effective to arrange the coil 34 that constitutes the second linear magnetic field generator 10 to extend not in the direction of the y-axis in the reference coordinate axes as shown in FIG. 3, but in the direction of the z-axis.

An advantage of a positional relation detecting system according to the second embodiment will be explained next. The positional relation detecting system according to the second embodiment has further advantages obtained by using the earth magnetism, in addition to the advantage in the first embodiment. Namely, by adopting the configuration using the earth magnetism as the first linear magnetic field, it is possible to omit the mechanism to generate the first linear magnetic field in the configuration, and it is possible to calculate the positional relation of the target coordinate axes with respect to the reference coordinate axes while reducing a load on the subject 1. Since the earth magnetism sensor 61 can be configured with an MI sensor, it can be made sufficiently compact. Therefore, additional arrangement of the earth magnetism sensor 61 does not increase load on the subject 1.

In addition, by adopting the configuration using the earth magnetism as the first linear magnetic field, an advantage in terms of reducing power consumption is obtained. Specifically, in the case of generating the first linear magnetic field with a coil or the like, an amount of the power consumption increases due to the electric current to be fed to the coil, however, such power consumption is not necessary if the earth magnetism is used, thereby realizing a system of low power consumption.

While the present invention has been explained above with the first and the second embodiment, the present invention should not be interpreted being limited to the above embodiments, and those skilled in the art can think of various embodiments, modifications, and like. For example, while in the first and the second embodiments, a case in which the second linear magnetic field generator 10 is used as the magnetic field generator has been explained, as it is easily understood from the above explanation, the first linear magnetic field generator 9 or/and the diffuse magnetic field generator 11 can be used as the magnetic field generator, and the first linear magnetic field or/and the diffuse magnetic field can be used as the magnetic field for position detection.

Moreover, it can be simply configured to perform the control by the magnetic-field strength controller 50 only before introducing the capsule endoscope 2 into the subject 1. In this case, the magnetic field sensor 13 can be removed from the outer surface of the subject 1 after the control by the magnetic-field strength controller 50 is once completed and the capsule endoscope 2 is introduced into the subject 1. Moreover, as a further simple configuration, the magnetic field sensor 16 provided in the capsule endoscope 2 before introduction into the subject 1 can be used to serve as a body-size information acquiring unit instead of the magnetic field sensor 13. Specifically, it can be configured such that the magnetic-field strength controller 50 performs the control based on the magnetic field strength detected by the capsule endoscope 2 that is temporarily fixed at a predetermined position on the outer surface of the subject 1.

Furthermore, while the magnetic field sensor 13 is used as an example of the body-size information detector, similarly, it is not limited to this configuration. The body-size information should be information that varies depending on the body size of the subject 1, and that is applicable to the calculation of strength of the magnetic field generated by the magnetic field generator, and the configuration of the body-size information detector can also take an arbitrary form as long as these conditions are satisfied. For example, information on height and weight of the subject 1 can be used as the body-size information. In this case, the magnetic-field strength database 51 stores correlation between height and weight of the subject 1 and the strength of the magnetic field generated by the magnetic field generator, thereby enabling the magnetic-field strength control by the magnetic-field strength controller 50.

Moreover, the detection subject can be other than the capsule endoscope 2 inside the subject 1. As is obvious from the above explanation, the present invention is applicable regardless of character of the detection subject. Specifically, the detection subject and the like can be an arbitrary object, as long as a position detecting apparatus is configured to include the magnetic field generator that generates the magnetic field for position detection, the magnetic field sensor that is arranged so as to be distant from the magnetic field generator for a distance that is equal to or more than the maximum value for the distance between the area in which the detection subject can be positioned (possible location area) and the magnetic field generator, and that detects the strength of the magnetic field for position detection, and the magnetic-field strength controller that controls the magnetic field generator based on the magnetic field strength detected by the magnetic field sensor.

INDUSTRIAL APPLICABILITY

As described above, the body-insertable apparatus system and the position detecting method according to the present invention is useful for a medical examination device to examine a subject portion while being introduced inside a human body, and is particularly suitable for generating a magnetic field for position detection having an optimal strength corresponding to a difference in body sizes of subjects.

The invention claimed is:

1. A body-insertable apparatus system comprising:
a body-insertable apparatus that is introduced into a subject and moves inside the subject,
the body-insertable apparatus including
a magnetic field sensor that detects strength of a magnetic field for position detection at a position at which the body-insertable apparatus is present, and
a radio transmitting unit that transmits a radio signal that contains information on the strength of the magnetic field detected by the magnetic field sensor; and
a position detecting apparatus that detects a position of the body-insertable apparatus inside the subject using the predetermined magnetic field for position detection, the position detecting apparatus including
a magnetic field generator that generates the magnetic field for position detection, and
a body-size information detector that is arranged at a predetermined position on the outer surface of the subject, and includes a magnetic field sensor unit that detects strength of the magnetic field for position detection at the arranged position as body-size information, the body-size information corresponding to a shape of an outer surface of the subject;
a magnetic-field strength controller that controls the strength of the magnetic field for position detection generated by the magnetic field generator, based on the body-size information.

2. The body-insertable apparatus system according to claim 1, wherein the magnetic-field strength controller controls a driving condition of the magnetic field generator so that the magnetic field for position detection has strength detectable by the magnetic field sensor in all areas in which the body-insertable apparatus can be positioned inside the subject, based on the body-size information.

3. The body-insertable apparatus system according to claim 1, wherein
the magnetic-field strength controller controls such that the magnetic field strength detected as the body-size information has strength detectable by the magnetic field sensor in the body-insertable apparatus.

4. The body-insertable apparatus system according to claim 1, wherein
the magnetic field generator includes a coil that generates a magnetic field according to power supplied by a predetermined power supply unit, and
the magnetic-field strength controller controls strength of the magnetic field for position detection by adjusting power to be supplied to the coil.

5. The body-insertable apparatus system according to claim 1, wherein
the magnetic field generator includes a coil that generates a magnetic field according to power supplied by a power supply unit constituted of any one of a primary cell and a secondary cell,
the body-insertable apparatus system further comprising
a power determining unit that determines whether the power supply unit is capable of supplying power for a predetermined period, the power corresponding to the magnetic field for position detection having the magnetic field strength acquired by the magnetic-field strength controller, and
a display unit that displays a determination result acquired by the power determining unit.

* * * * *